US005837241A

United States Patent [19]
Ferrara et al.

[11] Patent Number: 5,837,241
[45] Date of Patent: Nov. 17, 1998

[54] METHOD OF TREATING HEART FAILURE USING LEUKEMIA INHIBITORY FACTOR ANTAGONISTS OPTIONALLY WITH ENDOTHELIN ANTAGONISTS

[75] Inventors: Napoleone Ferrara, San Francisco; Kathleen King, Pacifica; Elizabeth Luis, San Francisco; Jennie P. Mather, Millbrae; Nicholas F. Paoni, Belmont, all of Calif.

[73] Assignee: Genentech, Inc., South San Francisco, Calif.

[21] Appl. No.: 693,826

[22] Filed: Jul. 26, 1996

Related U.S. Application Data

[63] Continuation of Ser. No. 428,002, Apr. 24, 1995, Pat. No. 5,573,762.

[51] Int. Cl.$^6$ .......................... A61K 39/395; C12N 5/12; C07K 16/18; C07K 16/22

[52] U.S. Cl. .................................. 424/136.1; 424/141.1; 424/145.1; 424/152.1; 424/156.1; 424/158.1; 435/332; 435/336; 530/387.1; 530/388.2; 530/388.24; 530/388.85; 530/389.2

[58] Field of Search ........................ 530/388.23, 388.24, 530/350, 300, 387.1, 388.2, 388.85, 389.2; 435/240.27, 172.2, 70.21, 332, 336; 514/9–11; 424/158.1, 145.1, 130.1, 141.1, 152.1, 156.1

[56] References Cited

U.S. PATENT DOCUMENTS

| | | | |
|---|---|---|---|
| 5,270,313 | 12/1993 | Burri et al. ............................ | 514/252 |
| 5,292,740 | 3/1994 | Burri et al. . | |
| 5,370,870 | 12/1994 | Wong et al. . | |

FOREIGN PATENT DOCUMENTS

| | | | |
|---|---|---|---|
| 6601386 A1 | 11/1993 | European Pat. Off. ...... | C07D 239/46 |
| 6633259 A1 | 6/1994 | European Pat. Off. ...... | C07D 401/12 |
| 6647449 A1 | 6/1994 | European Pat. Off. ....... | A61K 38/03 |
| 92/22653 | 12/1992 | WIPO ........................... | C12N 15/13 |
| 93/21219 | 10/1993 | WIPO ............................. | C07K 7/06 |
| 93/23556 | 11/1993 | WIPO ............................ | C12P 21/08 |
| WO 95/08550 | 3/1995 | WIPO . | |

OTHER PUBLICATIONS

Harris TIBTECH 11:42–44, 1993.
Pepper J. Cell Sci. 108: 78–83, 1995.
Metcalf & Gearing PNAS 86: 5948–5952, 1989.
Shen & Leder PNAS 89: 8240–8244, 1992.
Gearing et al., "Leukemia Inhibitory Factor Receptor is Structurally related to the IL–6 Signal Transducer, gp130" *EMBO Journal* 10 (10) :2839–2848 (1991).
Ito et al., "Endothelin $ET_A$ Receptor Antagonist Blocks Cardiac Hypertrophy Provoked by Hemodynamic Overload" *Circulation* 89 (5) :2198–2203 (May 1994).
Pennica et al., "Cardiotrophin–1. Biological Activities and Binding to the Leukemia Inhibitory Factor Receptor/gp130 Signaling Complex" *Journal of Biological Chemistry* 270 (1) :10915–10922 (1995).

Alphonso et al., "Neutralizing Monoclonal Antibodies to Human Leukemia Inhibitory Factor (LIF)" *1991 Annual Meeting Abstracts* p. 49 (1991).
Arai et al., "Cloning and Expression of a cDNA Encoding an Endothelin Receptor" *Nature* 348 (20) :730–732 (1990).
Battistini et al., "Growth Regulatory Properties of Endothelins" *Peptides* 14:385–399 (1993).
Boheler et al., "Gene Expression in Cardiac Hypertrophy" *TCM* 2 (5) :176–182 (1992).
Brouty–Boye et al., "α–Smooth Muscle Actin Expression in Cultured Cardiac Fibroblasts of Newborn Rats" *In Vitro Cell. Dev. Biol.* 28A:293–296 (Apr. 1992).
Chien, "Molecular Advances in Cardiovascular Biology" *Science* 260 :916–917 (May 14, 1993).
Chien et al., "Regulation of Cardiac Gene Expression During Myocardial Growth and Hypertrophy: Molecular Studies of an Adaptive Physiologic Response" *FASEB J.* 5:3037–3046 (1991).
Chien et al., "Transcriptional Regulation During Cardiac Growth and Development" *Annu. Rev. Physiol.* 55 :77–95 (1993).
Davis et al., "The Molecular Biology of the CNTF Receptor"*Curr. Opin. Cell Biol.* 5 :281–285 (1993).
Doetschman et al., "The In Vitro Development of Blastocyst–Derived Embryonic Stem Cell Lines: Formation of Visceral Yolk Sac, Blood Islands and Myocardium" *J. Embryol. Exp. Morphol.* 87 :27–45 (1985).
Elias et al., "Cytokine–Cytokine Synergy and Protein Kinase C in the Regulation of Lung Fibroblast Leukemia Inhibitory Factor" *American Journal of Physiology* 266 (10) : L426–L435 (1994).
Gough, "Molecular Genetics of Leukemia Inhibitory Factor (LIF) and Its Receptor" *Growth Factors* 7:175–179 (1992).
Hamilton et al., "Induction of Leukemia Inhibitory Factor in Human Synovial Fibroblasts by IL–1 and Tumor Necrosis Factor–α" *Journal of Immunology* 150 (4) :1496–1502 (Feb. 15, 1993).
Hilal–Dandan et al., "Coupling of the Type A Endothelin Receptor to Multiple Responses in Adult Rat Cardiac Myocytes" *Molecular Pharmacology* 45 :1183–1190 (1994).
Hilton et al., "Leukemia Inhibitory Factor: A Biological Perspective" *J. Cell Biochem.* 46 :21–26 (1991).
Ihara et al., "Biological Profiles of Highly Potent Novel Endothelin Antagonists Selective for the $ET_A$ Receptor" *Life Sciences* 50 :247–255 (1992).
Ihara et al., "An Endothelin Receptor ($ET_A$) Antagonist Isolated From Streptomyces Misakiensis" *Biochemical and Biophysical Research Communications* 178 (1) :132–137 (Jul. 15, 1991).

(List continued on next page.)

*Primary Examiner*—Toni R. Scheiner
*Assistant Examiner*—Nancy A. Johnson
*Attorney, Agent, or Firm*—Janet E. Hasak; Timothy E. Torchia; Deirde L. Conley

[57] ABSTRACT

A leukemia inhibitory factor antagonist, alone or in combination with an endothelin antagonist, may be used for treatment of heart failure. The antagonist(s) are administered in a chronic fashion, in therapeutically effective amounts, to achieve this purpose.

4 Claims, 8 Drawing Sheets

OTHER PUBLICATIONS

Inoue et al., "The Human Endothelin Family: Three Structurally and Pharmacologically Distinct Isopeptides Predicted by Three Separate Genes" *Proc. Natl. Acad. Sci. USA* 86 :2863–2867 (Apr. 1989).

Ito et al., "Endothelin–1 Induces Hypertrophy With Enhanced Expression of Muscle–Specific Genes in Cultured Neonatal Rat Cardiomyocytes" *Circulation Research* 69 (1):209–215 (Jul. 1991).

Iwaki et al., "α–and β–Adrenergic Stimulation Induces Distinct Patterns of Immediate Early Gene Expression in Neonatal Rat Myocardial Cells" *Journal of Biological Chemistry* 265 (23) :13809–13817 (1990).

Jones et al., "Endothelin Stimulates Multiple Responses in Isolated Adult Ventricular Cardiac Myocytes" *American Journal of Physiology* 263 (32) :H1447–H1454 (1992).

Katz, "Heart Failure" *Physiology of the Heart* pp. 638–668 (1992).

Kim et al., "Detection of Human Leukemia Inhibitory Factor by Monoclonal Antibody Based ELISA" *Journal of Immunological Methods* 156:9–17 (1992).

Kishimoto et al., "Cytokine Signal Transduction" *Cell* 76:253–262 (1994).

Kishimoto et al., "Interleukin–6 and Its Receptor: A Paradigm for Cytokines" *Science* 258:593–597 (Oct. 23, 1992).

Kitamura et al., "Multimeric Cytokine Receptors" *TEM* 5 (1) :8–14 (1994).

Kurzrock et al., "LIF: Not Just a Leukemia Inhibitory Factor" *Endocrine Reviews* 12 (3) :208–217 (1991).

Libby, "Long–Term Culture of Contractile Mammalian Heart Cells in a Defined Serum–Free Medium that Limits Non–Muscle Cell Proliferation" *J. Mol. Cell. Cardiol.* 16: 803–811 (1984).

Long et al., "A Growth Factor for Cardiac Myocytes is Produced by Cardiac Nonmyocytes" *Cell Reg.* 2:1081–1095 (Dec. 1991).

Lorenzo et al., "Tumor Necrosis Factor α Stimulates Production of Leukemia Inhibitory Factor in Human Dermal Fibroblast Cultures" *Clinical Immunology and Immunopathology* 70 (3) :260–265 (Mar. 1994).

Metcalf, "Leukemia Inhibitory Factor—A Puzzling Polyfunctional Regulator" *Growth Factors* 7 :169–173 (1992).

Miller–Hance et al., "In Vitro Chamber Specification During Embroyonic Stem Cell Cardiogenesis" *The Journal of Biological Chemistry* 268 (33) :25244–25252 (Nov. 25, 1993).

Nag "Study of Non–Muscle Cells of the Adult Mammalian Heart: A Fine Structural Analysis and Distribution" *Cytibios* 28: 41–61 (1980).

Pennica et al., "Expression Cloning of Cardiotrophin 1, a Cytokine That Induces Cardiac Myocyte Hypertrophy" *Proceedings of the National Academy of Sciences, USA* 92:1142–1146 (Feb. 1995).

Rastetter et al., "Monoclonal Antibodies Stage a Comeback" *Bioventure View* 19 (11) :1–7 (Nov. 1995).

Robbins et al., "Mouse Embryonic Stem Cells Express the Cardiac Myosin Heavy Chain Genes During Development in Vitro" *Journal of Biological Chemistry* 265 (20):11905–11909 (1990).

Shubeita et al., "Endothelin Induction of Inositol Phospholipid Hydrolysis, Sarcomere Assembly, and Cardiac Gene Expression in Ventricular Myocytes" *Journal of Biological Chemistry* 265 (33) :20555–20562.

Simpson et al., "Differentiation of Rat Myocytes in Single Cell Cultures with and without Proliferating Nonmyocardial Cells" *Circ. Res.* 50 (1) :101–116 (1982).

Simpson et al., "Myocyte Hypertrophy in Neonatal Rat Heart Cultures and Its Regulation by Serum and by Catecholamines" *Circ. Res.* 51(6) :787–801 (1982).

Suzuki et al., "Endothelin–1 Stimulates Hypertrophy Contractility of Neonatal Rat Cardiac Myocytes in a Serum–Free Medium. II" *Journal of Cardiovascular Pharmacology* 17 (7) : S182–S186 (1991).

Webb et al., "The Endothelin Receptor Antagonist, BQ–123, Inhibits Angiothensin II–induced Contractions in Rabbit Aorta" *Biomedical and Biophysical Research Communications* 185 (3) :887–892 (Jun. 30, 1992).

Wei et al., "Endothelin in Human Congestive Heart Failure" *Circulation* 89 (4) :1580–1586 (Apr. 1994).

Yamamori et al., "The Cholingergic Neuronal Differentiation Factor from Heart Cells is Identical to Leukemia Inhibitory Factor" *Science* 246 :1412–1416 (1989).

Yanagisawa and Masaki, "Molecular Biology and Biochemistry of the Endothelins" *TiPS* 10 :374–378 (Sep. 1989).

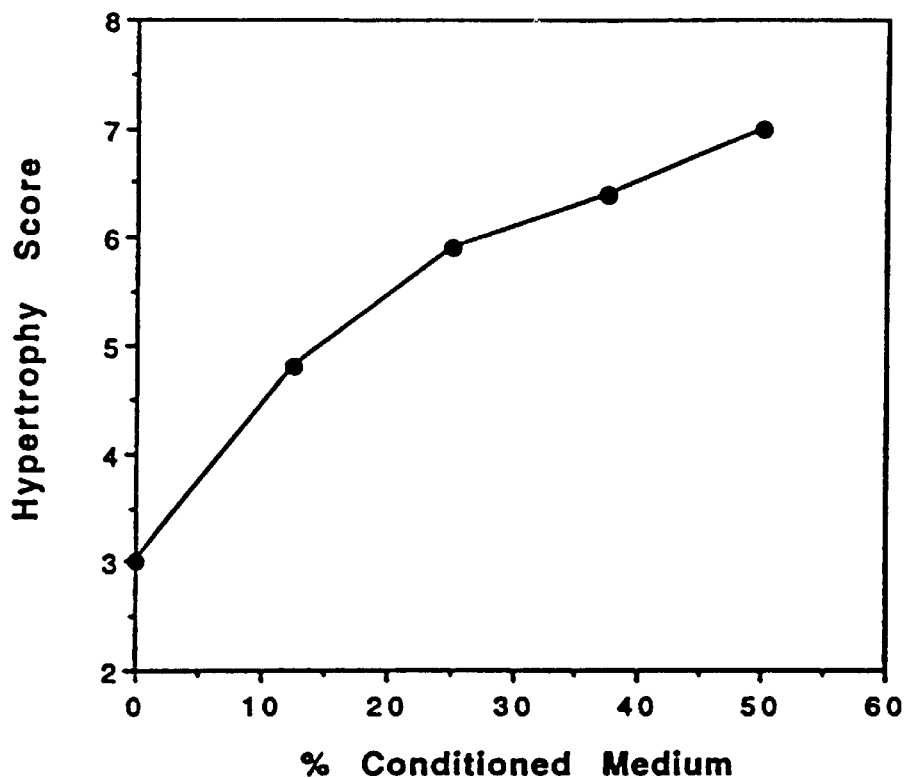
FIG. IA
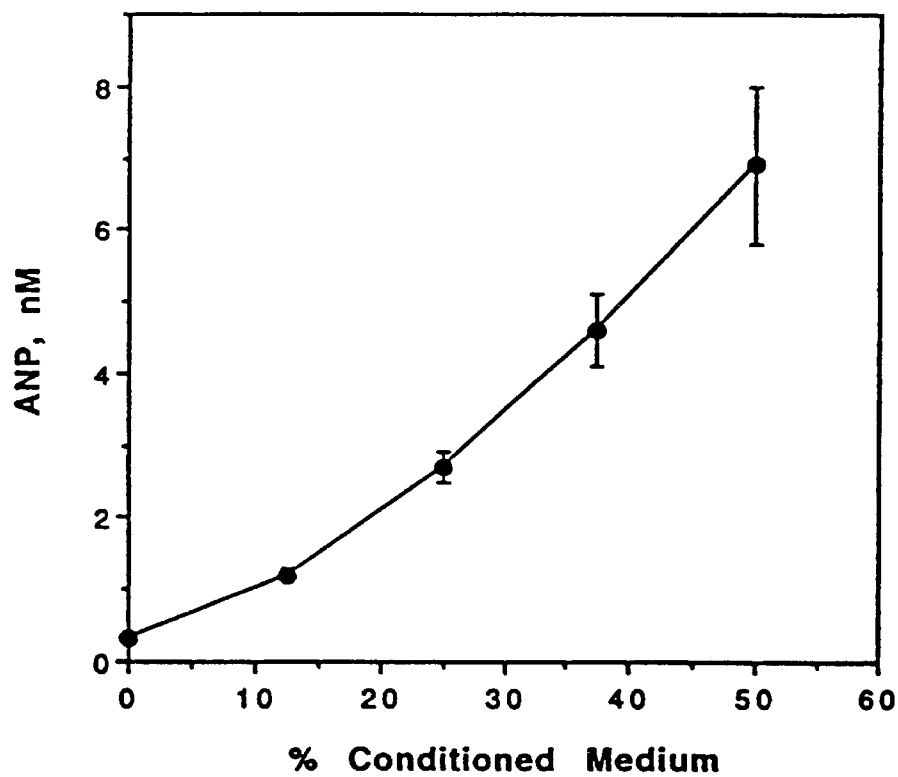
FIG. IB

METHOD OF TREATING HEART FAILURE USING LEUKEMIA INHIBITORY FACTOR ANTAGONISTS OPTIONALLY WITH ENDOTHELIN ANTAGONISTS

This is a continuation of co-pending application Ser. No. 08/428,002 filed Apr. 24, 1995, U.S. Pat. No. 5,573,762, which application is incorporated herein by reference and to which application priority is claimed under 35 USC §120.

BACKGROUND OF THE INVENTION

1. Field of the Invention

This application relates to a method for modulating cardiac function in the treatment of heart disorders.

2. Background of the Invention

Heart failure affects approximately three million Americans, developing in about 400,000 each year. It is currently one of the leading admission diagnoses in the U.S. Recent advances in the management of acute cardiac diseases, including acute myocardial infarction, are resulting in an expanding patient population that will eventually develop chronic heart failure.

Current therapy for heart failure is primarily directed to using angiotensin-converting enzyme (ACE) inhibitors and diuretics. While prolonging survival in the setting of heart failure, ACE inhibitors appear to slow the progression towards end-stage heart failure, and substantial numbers of patients on ACE inhibitors have functional class III heart failure. Moreover, ACE inhibitors consistently appear unable to relieve symptoms in more than 60% of heart failure patients and reduce mortality of heart failure only by approximately 15–20%. Heart transplantation is limited by the availability of donor hearts. Further, with the exception of digoxin, the chronic administration of positive inotropic agents has not resulted in a useful drug without accompanying adverse side effects, such as increased arrhythmogenesis, sudden death, or other deleterious side effects related to survival. These deficiencies in current therapy suggest the need for additional therapeutic approaches.

A large body of data suggests that pathological hypertrophy of cardiac muscle in the setting of heart failure can be deleterious, characterized by dilation of the ventricular chamber, an increase in wall tension/stress, an increase in the length vs. width of cardiac muscle cells, and an accompanying decrease in cardiac performance and function. In fact, the effects of ACE inhibitors have been purported not only to unload the heart, but also to inhibit the pathological hypertrophic response that has been presumed to be linked to the localized renin-angiotensin system within the myocardium.

On a cellular level, the heart functions as a syncytium of myocytes and surrounding support cells, called non-myocytes. While non-myocytes are primarily fibroblast/mesenchymal cells, they also include endothelial and smooth muscle cells. Indeed, although myocytes make up most of the adult myocardial mass, they represent only about 30% of the total cell numbers present in heart. Because of their close relationship with cardiac myocytes in vivo, non-myocytes are capable of influencing myocyte growth and/or development. This interaction may be mediated directly through cell-cell contact or indirectly via production of a paracrine factor. Such association in vivo is important since both non-myocyte numbers and the extracellular matrix with which they interact are increased in myocardial hypertrophy and in response to injury and infarction. These changes are associated with abnormal myocardial function.

Cardiac myocytes are unable to divide shortly after birth. Further growth occurs through hypertrophy of the individual cells. Cell culture models of myocyte hypertrophy have been developed to understand better the mechanisms for cardiac myocyte hypertrophy. Simpson et al., *Circ. Res.,* 51: 787–801 (1982); Chien et al., *FASEB J.,* 5: 3037–3046 (1991). Most studies of heart myocytes in culture are designed to minimize contamination by non-myocytes. See, for example, Simpson and Savion, *Cir. Cres.,* 50: 101–116 (1982); Libby, *J. Mol. Cell. Cardiol.,* 16: 803–811 (1984); Iwaki et al., *J. Biol. Chem.,* 265: 13809–13817 (1990).

Hypertrophy of adult cardiac ventricular myocytes is a response to a variety of conditions which lead to chronic overload. This response is characterized by an increase in myocyte cell size and contractile protein content without concomitant cell division, and activation of embryonic genes, including the gene for atrial natriuretic peptide (ANP). Chien et al., supra. Adult myocyte hypertrophy is initially beneficial as a short term response to impaired cardiac function by permitting a decrease in the load on individual muscle fibers. With severe, long-standing overload, however, the hypertrophied cells begin to deteriorate and die. Katz, "Heart failure," in Katz AM, ed., *Physiology of the Heart* (New York: Raven Press; 1992) pp. 638–668.

Endothelial cells, smooth muscle cells and fibroblast/mesenchymal cells exist in close contact with myocytes in the heart. Nag, *Cytobios.,* 28: 41–61 (1980). In vitro studies have indicated that paracrine factors produced by these "non-myocyte" supporting cells may be involved in the development of hypertrophy. The identification of such factors remains a major pursuit in cardiac biology and medicine. Chien et al., *Science,* 260: 916–917 (1993). See also Chien et al., *Annu. Rev. Physiol.,* S5: 77–95. (1993), regarding the use of an in vitro assay system for myocardial cell hypertrophy to isolate and characterize novel activities that might mediate this important physiological response.

Cell culture models have been developed to study hypertrophy and its causes. Thus, for example, totipotent mouse embryonic stem cells differentiate into multicellular, cystic embryoid bodies when cultured in the absence of a fibroblast feeder layer or with the removal of leukemia inhibitory factor (LIF). Robbins et al., *J. Biol. Chem.,* 265: 11905–11909 (1990). Since these embryoid bodies spontaneously beat and display cardiac-specific markers (Robbins et al., supra; Doetschman et al., *J. Embryol. Exp. Morphol.,* 87: 27–45 [1985]; Miller-Hance et al., *J. Biol. Chem.,* 268: 25244–25252 [1993]), they might serve as a valuable source of factors that can induce a hypertrophic response in vitro. Chien, *Science,* supra; Miller-Hance et al., supra.

Further, Long et al., *Cell Reg.,* 2: 1081–1095 (1991), discovered that cultured neonatal rat cardiac non-myocytes, which were primarily fibroblast-like cells, produced an unidentified protein that also induced hypertrophy of cardiac myocytes in vitro. This factor bound to heparin-sepharose, failed to stimulate phosphoinositol hydrolysis, and had an apparent molecular weight of 45 to 50 kD. Experiments with neutralizing antisera to platelet-derived growth factor, tumor necrosis factor alpha, acidic and basic fibroblast growth factors and transforming growth factor beta 1, eliminated these growth factors as possible candidates.

Endothelin has been shown to affect the cells in the heart both in vivo and in vitro. In vivo endothelin is present in both atrial and ventricular myocardium in healthy and failing hearts and enhances myocardial inotropic activity, vascular smooth muscle proliferation and coronary vasoconstriction. Wei et al., *Circulation*, 89: 1580–1586 (1994). In vitro endothelin stimulates multiple cell-signalling pathways in cultured adult cardiac myocytes. Hilal-Dandan et al., *Mol. Pharm.*, 45: 1183–1190 (1994); Jones et al., *Am. J. Physiol. (Heart Circ. Physiol.* 32) 263: H1447-H1454 [1992). Several investigators have shown that endothelin-1, which is known to be produced in endothelial cells, induces hypertrophy of cardiac myocytes in vitro. Shubeita et al., *J. Biol. Chem.*, 265: 20555–20562 (1990); Ito et al., *Circ Res.*, 69: 209–215 (1991); Suzuki et al., *J. Cardiovasc. Pharmacol.*, 17 Suppl 7: S182–S186 (1991). See also U.S. Pat. No. 5,344,644 issued Sep. 6 1994.

LIF, also known as leukocyte inhibitory factor, differentiation-inducing factor (DIF, D-factor), hepatocyte-stimulating factor (HSF-II HSF-III), and melanoma-derived LPL inhibitor (MLPLI), depending on its particular activity or effect (Hilton et al., *J. Cell. Biochem.*, 46: 21–26 [1991]), has also been identified as the cholinergic neuronal differentiation factor (CDF) from rat neonatal heart cell cultures with both myocytes and non-myocytes. Yammamori et al., *Science*, 246: 1412–1416 (1989). Additionally, LIF has been found to be useful for the protection, inhibition, and prevention of the deleterious effects of reactive oxygen species, including myocardial infarcts and protection of ischemic tissues. U.S. Pat. No. 5,370,870. Finally, LIF and cardiotrophin-1 (CT-1), another member of the family of proteins that bind to GH/cytokine receptors, show the most potent hypertrophy activity of that family of proteins on neonatal rat cardiac myocytes in culture, and they also induce a similar morphology. Pennica et al., *Proc. Natl. Acad. Sci. USA*, 92: 1142–1146 (1995).

SUMMARY OF THE INVENTION

It has now been shown herein that non-myocytes produce hypertrophic factors that are identified as LIF and endothelin. Accordingly, the invention provides, in one aspect, a method for treating a mammal experiencing heart failure to prevent or lessen hypertrophy comprising administering chronically to a mammal in need of such treatment a therapeutically effective amount of a LIF antagonist.

In another aspect, the invention provides a method for treating a mammal experiencing heart failure to prevent or lessen hypertrophy comprising administering chronically to a mammal in need of such treatment a therapeutically effective amount of a LIF antagonist and an endothelin antagonist.

In a still further aspect, the invention provides a composition comprising a LIF antagonist and an endothelin antagonist in a pharmaceutically acceptable carrier.

BRIEF DESCRIPTION OF THE DRAWINGS

FIG. 1 discloses the effect of non-myocyte-conditioned medium (NCM) from rat neonates on cultured rat neonatal cardiac myocyte size, expressed as hypertrophy score, and ANP production. Myocytes were treated with NCM for 48 hours. The culture medium was assayed for ANP (FIG. 1B), and the cells were stained with crystal violet and scored for hypertrophy (FIG. 1A). Untreated controls were scored as 3 and maximally hypertrophied cells as 7. The data represent the mean and standard error of three experiments done in duplicate and assayed in duplicate.

DETAILED DESCRIPTION OF THE PREFERRED EMBODIMENTS

I. Definitions

Figure 2:
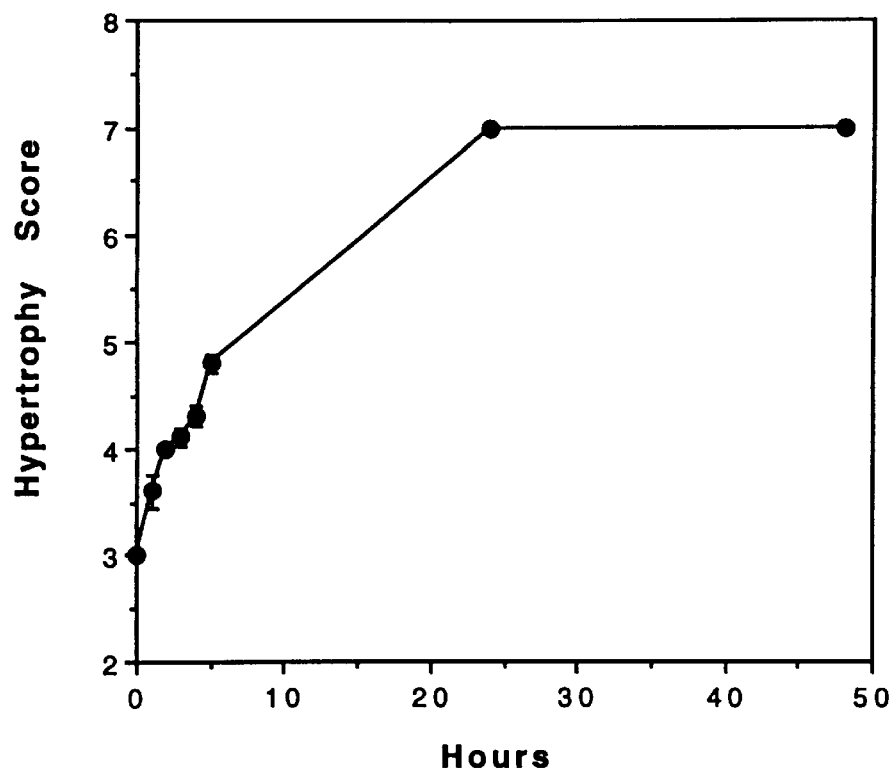
FIG. 2 discloses the time course of appearance of hypertrophy activity in rat neonatal cardiac NCM. Passage-one rat neonatal cardiac non-myocytes were cultured in 10% serum containing medium for 5 days, then washed twice in serum-free medium. Assay medium was added and aliquots were removed after culture for the times indicated. The data represent the mean and standard error of three experiments done in duplicate and assayed in duplicate.

In general, the following words or phrases have the indicated definition when used in the description, examples, and claims:

"LIF antagonist" and "endothelin antagonist" as used herein mean any molecule which blocks or prevents the interaction between LIF or endothelin and their respective receptors. Such antagonists accomplish this effect in various ways. For instance, one class of antagonists will bind to LIF or endothelin with sufficient affinity and specificity to neutralize LIF or endothelin such that they have no effect on their respective receptors. Included within this group of antagonists are antibodies. Another class of antagonists are molecules based on an interaction between the LIF or endothelin and their respective receptors. Such molecules include fragments of the LIF or endothelin receptor or small bioorganic molecules, e.g. peptidomimetics, that will prevent the interaction between the respective receptor and the LIF or endothelin. LIF is described by, e.g., Metcalf, *Growth Factors,* 7: 169–173 (1992) and Kurzrock et al., *Endocrine Reviews,* 12: 208–217 (1991). Activation of the LIF receptor has been shown to stimulate intracellular tyrosine kinases. Kishimoto et al., *Science,* 258:593–597 (1992). Several laboratories have shown that fibroblasts in culture can produce LIF (Elias et al., *Am. J. Physiol. (Lung Cell. Mol. Physiol.* 10). 266: L426–L435 [1994]; Lorenzo et al., *Clin. Immunol. Immunopath.,* 70: 260–265 [1994]; Hamilton et al. *J. Immunol.,* 150: 1496–1502 [1993]).

There are three endothelin-related peptides, endothelin-1, -2, and -3. Inoue et al., *Proc. Natl. Acad. Sci. USA,* 86: 2863–2867 (1989). Endothelin-1 is a 21 amino acid peptide which is a potent venous and arterial vasoconstrictor. The mature biologically active peptide is a proteolytic product of the 38–39 amino acid molecule "Big Endothelin." Yanagisawa and Masaki, *Trends Pharm. Sci.,* 10: 374–378 (1989). Endothelin has been shown to induce protein tyrosine phosphorylation in aortic smooth muscle cells, mesangial cells, and osteoblast-like cells (Battistini et al., *Peptides,* 14: 385–399 [1993]), but in neonatal rat myocytes in culture, endothelin, like the alpha adrenergic agents, stimulates phosphoinositide hydrolysis and the accumulation of diacylglycerol. Shubeita et al., supra, and Ito et al., supra. Endothelins are produced by vascular endothelial cells, epithelial cells, macrophages, fibroblasts and many other types of cells. Battistini et al., supra.

The antagonists to these molecules influence cardiac growth or hypertrophy activity, as measured, e.g., by atrial natriuretic peptide (ANP) release or by the myocyte hypertrophy assay described herein using a specific plating medium and plating density, and preferably using crystal violet stain for readout. The desired function of an antagonist is to provide the result desired in the continuum of equilibria between growing and shrinking of cardiac muscle tissue.

Non-limiting examples of LIF antagonists include antibodies, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Another class of antagonists blocks or prevents intracellular or membrane associated events occurring between the respective receptor and the LIF or endothelin.

In a preferred embodiment the antagonist is an antibody, which antibody has the desirable properties of binding to LIF or endothelin and preventing its interaction with its respective receptor. Such antibodies are preferably generated against recombinant human LIF that are neutralizing against the hypertrophy induced by both human and mouse LIF, but not against CT-1-, endothelin-, or phenylephrine-induced hypertrophy. For example, in the example below, three monoclonal antibodies meeting these criteria were identified, each of which recognizes a different antigenic determinant on recombinant human LIF. All three of these antibodies neutralized the myocyte hypertrophy induced by mouse and human LIF and two of them were equipotent in inhibiting the hypertrophy induced by NCM. One or more of these antibodies are described in WO 93/23556 published 25 Nov. 1993; Kim et al., *J. Immunol. Meth.,* 156: 9–17 (1992); and Alphonso et al., *J. Leukocyte Biology* (Abstracts of the 28th National Meeting of the Society for Leukocyte Biology, vol. 0, no. SP.2 (1991) (NY, N.Y., p. 49) (Mabs D4.16.9, D25.1.4, and D62.3.2).

In another preferred aspect, the antagonist is a soluble receptor based on the primary structure of the endothelin or LIF receptor which has the desirable quality of preventing the interaction of the respective receptor with the LIF or endothelin. In another preferred embodiment, the antagonist is a bioorganic molecule, usually an orally active compound that is based on molecular modeling studies, which is capable of preventing the interaction between the LIF or endothelin and its respective receptor. In another aspect of the invention, the antagonist is a transcriptional regulator of LIF or endothelin expression in vivo.

Non-limiting examples of endothelin antagonists include antagonists against any type of endothelin, including endothelin-1, -2, and -3, big endothelin, or combinations thereof. Such antagonists include not only antibodies, but also peptides that are selective blockers of endothelin A or endothelin B receptor or both. As pointed out above, the endothelin A receptor is selective for endothelin-1 and endothelin-2 over endothelin-3. The endothelin B receptor binds all three with the same affinity. One example is BQ-123 (Ihara et al., *Life Science,* 50: 247–250 [1992]; JP 51–94254A published Aug. 3, 1993; Webb et al., *Biochem. Biophys. Res. Comm.,* 185: 887–892 [1992]), a cyclic pentapeptide that is a potent and specific blocker of endothelin A receptors and blocks only the hypertrophic activity induced by endothelin-1, not CT-1, mouse LIF, or phenylephrine. Another example is the parent compound to BQ-123 described by Ihara et al., *Biochim. Biophys. Res. Comm.,* 178: 132–137 (1991). Further examples include those described in EP 647,236; EP 647,449; EP 633,259 (phenylsulfonyl amino-pyrimidine derivatives); EP 601,386 (sulfonamide compounds); U.S. Pat. No. 5,292,740 (phenylsulfonamidopyrimidines);and U.S. Pat. No. 5,270, 313 (phenyl-sulfonyl-aminopyrimidinederivatives).

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000.daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., *J. Mol. Biol.,* 186: 651–663 [1985]; Novotny and Haber, *Proc. Natl. Acad. Sci. USA,* 82: 4592–4596 [1985]).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. [1991]). The constant domains are not involved directly in binding an antibody to an antigen, but exhibit various effector functions, such as participation of the antibody in antibody-dependent cellular toxicity.

Papain digestion of antibodies produces two identical antigen- binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG-1, IgG-2, IgG-3, IgG-4, IgA-1, and IgA-2. The heavy-chain constant domains that correspond to the different classes of immunoglobulins are called ;α, δ, ε, γ, and μ, respectively. The subunit structures and three-dimensional configurations of different classes of immunoglobulins are well known.

The term "antibody" is used in the broadest sense and specifically covers single monoclonal antibodies (including agonist and antagonist antibodies) and antibody compositions with polyepitopic specificity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins.

The monoclonal antibodies herein include hybrid and recombinant antibodies produced by splicing a variable (including hypervariable) domain of an anti-LIF or anti-endothelin antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. [See, e.g., Cabilly et al., U.S. Pat. No. 4,816,567; Mage and Lamoyi, in *Monoclonal Antibody Production Techniques and Applications*, pp.79–97 (Marcel Dekker, Inc., New York, 1987).]

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature*, 256: 495 (1975), or may be made by recombinant DNA methods (cabilly et al., supra).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., *Proc. Natl. Acad. Sci. USA*, 81: 6851–6855 [1984]).

"Humanized" forms of non-human (e.g., murine) antibodies are specific chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., *Nature*, 321: 522–525 (1986); Reichmann et al., *Nature*, 332: 323–329 (1988); and Presta, *Curr. Op. Struct. Biol.*, 2: 593–596 (1992).

"Non-immunogenic in a human" means that upon contacting the polypeptide in a pharmaceutically acceptable carrier and in a therapeutically effective amount with the appropriate tissue of a human, no state of sensitivity or resistance to the polypeptide is demonstrable upon the second administration of the polypeptide after an appropriate latent period (e.g., 8 to 14 days).

"Heart failure" refers to an abnormality of cardiac function where the heart does not pump blood at the rate needed for the requirements of metabolizing tissues. The heart failure can be caused by any number of factors, including ischemic, congenital, rheumatic, or idiopathic forms.

"Treatment" refers to both therapeutic treatment and prophylactic or preventative measures, wherein the object is to prevent or slow down (lessen) hypertrophy. Those in need of treatment include those already with the disorder as well as those prone to have the disorder or those in which the disorder is to be prevented. The hypertrophy may be from any cause, including idiopathic, candiotrophic, or myotrophic causes, or as a result of ischemia or ischemic insults such as myocardial infarction. Typically, the treatment is performed to stop or slow the progression of hypertrophy, especially after heart damage, such as from ischemia, has occurred. Preferably, for treatment of myocardial infarctions, the agent(s) is given immediately after the myocardial infarction, to prevent or lessen hypertrophy.

"Chronic" administration refers to administration of the agent(s) in a continuous mode as opposed to an acute mode, so as to maintain the initial anti-hypertrophic effect for an extended period of time.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

As used herein, "ACE inhibitor" refers to angiotensin-converting enzyme inhibiting drugs which prevent the conversion of angiotensin I to angiotensin II. The ACE inhibitors may be beneficial in congestive heart failure by reducing systemic vascular resistance and relieving circulatory congestion. The ACE inhibitors include but are not limited to those designated by the trademarks Accupril® (quinapril), Altace®0 (ramipril), Capoten® (captopril), Lotensine® (benazepril), Monopril® (fosinopril), Prinivil® (lisinopril), Vasotec® (enalapril), and Zestril® (lisinopril). One example of an ACE inhibitor is that sold under the trademark Capoten®. Generically referred to as captopril, this ACE inhibitor is designated chemically as 1-[(2S)-3-mercapto-2-methylpropionyl]-L-proline.

II. Modes for Practicing the Invention

The invention constitutes a method for treating a mammal having heart failure, wherein a therapeutically effective amount of a LIF antagonist is chronically administered to the mammal. Optionally, the LIF antagonist is chronically administered in combination with an effective amount of an antagonist to endothelin. Additional optional components include a cardiotrophin inhibitor such as a CT-1 antagonist, an ACE inhibitor, such as captopril, and/or human growth hormone and/or IGF-I in the case of congestive heart failure, or with another anti-hypertrophic or myocardiotrophic factor in the case of other types of heart failure or cardiac disorder.

1. Preparation and Identification of Antagonists

A. General Preparation

Antagonists to LIF and endothelin can be prepared by using the predicted family of receptors for endothelin or for LIF. The endothelin A receptor is selective for endothelin-1 and endothelin-2 over endothelin 3. The endothelin B receptor binds all three with the same affinity. Arai et al., *Nature*, 348: 730–735 (1990). LIF, as well as ciliary neurotrophic factor (CNTF), interleukin-6 (IL-6), interleukin-11 (IL-11), CT-1, and oncostatin M (OSM), use related receptor signaling proteins including GP130 that are members of the GH/cytokine receptor family. Kishimoto et al., *Cell*, 76: 253–262 (1994); Kitamura et al., *Trends Endocrinol. Metab.*, 5: 8–14 (1994); Davis and Yancopoulos, *Curr. Opin. Cell Biol.*, 5: 281–285 (1993); Pennica et al., supra.

The receptors for LIF and endothelin can be expression cloned from their respective families; then a soluble form of the receptor is made by identifying the extracellular domain and excising the transmembrane domain therefrom. The soluble form of the receptor can then be used as an antagonist, or the receptor can be used to screen for small molecules that would antagonize LIF or endothelin activity, respectively.

Alternatively, variants of native LIF or endothelin are made that act as antagonists. The receptor binding site(s) of LIF and endothelin can be determined by binding studies and one or more of them eliminated by standard techniques (deletion or radical substitution of appropriate nucleic acids) so that the molecule acts as an antagonist. Antagonist activity can be determined by several means, including the hypertrophy assay described herein.

B. Antibody Preparation (i) Starting Materials and Methods

Immunoglobulins (Ig) and certain variants thereof are known and many have been prepared in recombinant cell culture. For example, see U.S. Pat. No. 4,745,055; EP 256,654; EP 120,694; EP 125,023; EP 255,694; EP 266,663; WO 88/03559; Faulkner et al., *Nature*, 298: 286 (1982); Morrison, *J. Immun.*, 123: 793 (1979); Koehler et al., *Proc. Natl. Acad. Sci. USA*, 77: 2197 (1980); Raso et al., *Cancer Res.*, 41: 2073 (1981); Morrison et al., *Ann. Rev. Immunol.*, 2: 239 (1984); Morrison, *Science*, 229: 1202 (1985); and Morrison et al., *Proc. Natl. Acad. Sci. USA*, 81: 6851 (1984). Reassorted immunoglobulin chains are also known. See, for example, U.S. Pat. No. 4,444,878; WO 88/03565; and EP 68,763 and references cited therein. The immunoglobulin moiety in the chimeras of the present invention may be obtained from IgG-1, IgG-2, IgG-3, or IgG-4 subtypes, IgA, IgE, IgD, or IgM, but preferably from IgG-1 or IgG-3.

(ii) Polyclonal antibodies

Polyclonal antibodies to LIF or endothelin are generally raised in animals by multiple subcutaneous (sc) or intraperitoneal (ip) injections of LIF or endothelin and an adjuvant. It may be useful to conjugate LIF or endothelin or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the LIF or endothelin polypeptide or fragment, immunogenic conjugates, or derivatives by combining 1 mg or 1 μg of the peptide or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer to LIF or endothelin or a fragment thereof. Animals are boosted until the titer plateaus. Preferably, the animal is boosted with the conjugate of the same LIF or endothelin or fragment thereof, but conjugated to a different protein and/or through a different cross-linking reagent. Conjugates also can be made in recombinant cell culture as protein fusions. Also, aggregating agents such as alum are suitably used to enhance the immune response.

(iii) Monoclonal antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, monoclonal antibodies using for practicing this invention may be made using the hybridoma method first described by Kohler and Milstein, *Nature*, 256: 495 (1975), or may be made by recombinant DNA methods (Cabilly et al., supra).

In the hybridoma method, a mouse or other appropriate host animal, such as a hamster, is immunized as hereinabove described to elicit lymphocytes that produce or are capable of producing antibodies that will specifically bind to the LIF or endothelin or fragment thereof used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59–103 [Academic Press, 1986]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA.

Culture medium in which hybridoma cells are growing is assayed for production of monoclonal antibodies directed against LIF or endothelin. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson and Pollard, *Anal. Biochem.*, 107: 220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxyapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5: 256–262 (1993) and Pluckthun, *Immunol. Revs.*, 130: 151–188 (1992).

The DNA also may be modified, for example, by substituting the coding sequence for human heavy- and light-chain constant domains in place of the homologous murine sequences (Morrison, et al., *Proc. Natl. Acad. Sci. USA*, 81: 6851 [1984]), or by covalently joining to the immunoglobulin coding sequence all or part of the coding sequence for a non-immunoglobulin polypeptide. In that manner, "chimeric" or "hybrid" antibodies are prepared that have the binding specificity of an anti-LIF or anti-endothelin monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a LIF or endothelin and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(iv) Humanized antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature 321, 522–525 [1986]; Riechmann et al., Nature 332, 323–327 [1988]; Verhoeyen et al., Science 239, 1534–1536 (1988]), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151: 2296 [1993]; Chothia and Lesk, J. Mol. Biol., 196: 901 [1987]). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89: 4285 [1992]; Presta et al., J. Immnol., 151: 2623 [1993]).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

(v) Human antibodies

Human monoclonal antibodies can be made by the hybridoma method. Human myeloma and mouse-human heteromyeloma cell lines for the production of human monoclonal antibodies have been described, for example, by Kozbor, J. Immunol. 133, 3001 (1984); Brodeur, et al., Monoclonal Antibody Production Techniques and Applications, pp.51–63 (Marcel Dekker, Inc., New York, 1987); and Boerner et al., J. Immunol., 147: 86–95 (1991).

It is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255–258 (1993); Bruggermann et al., Year in Immuno., 7: 33 (1993).

Alternatively, the phage display technology (McCafferty et al., Nature, 348: 552–553 [1990]) can be used to produce human antibodies and antibody fragments in vitro, from immunoglobulin variable (V) domain gene repertoires from non-immunized donors. According to this technique, antibody V domain genes are cloned in-frame into either a major or minor coat protein gene of a filamentous bacteriophage, 'such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson and Chiswell, Curr. Op. Struct. Biol., 3: 564–571 (1993). Several sources of V-gene segments can be used for phage display. Clackson et al., Nature, 352: 624–628 (1991) isolated a diverse array of anti-oxazolone antibodies from a small random combinatorial library of V genes derived from the spleens of immunized mice. A repertoire of V genes from non-immunized human donors can be constructed and antibodies to a diverse array of antigens (including self-antigens) can be isolated essentially following the techniques described by Marks et al., J. Mol. Biol., 222: 581–597 (1991), or Griffith et al., EMBO J., 12: 725–734 (1993).

In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., Bio/Technology, 10: 779–783 [1992]). In this method, the affinity of "primary" human antibodies obtained by phage display can be improved by sequentially replacing the heavy and light chain V region genes with repertoires of naturally occurring variants (repertoires) of V domain genes obtained from non-immunized donors. This technique allows the production of antibodies and antibody fragments with affinities in the nM range. A strategy for making very large phage antibody repertoires has been described by Waterhouse et al., Nucl. Acids Res., 21: 2265–2266 (1993).

Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. , the epitope governs (imprints) the choice of partner. When the process is repeated in order to replace the remaining rodent V domain, a human antibody is obtained (see PCT WO 93/06213, published 1 Apr. 1993). Unlike traditional humanization of rodent antibodies by CDR grafting, this technique provides completely human antibodies, which have no framework or CDR residues of rodent origin.

(vi) Bispecific Antibodies

Bispecific antibodies are monoclonal, preferably human or humanized, antibodies that have binding specificities for at least two different antigens. In the present case, one of the binding specificities is for a LIF, the other one is for an endothelin. Methods for making bispecific antibodies are known in the art.

Traditionally, the recombinant production of bispecific antibodies is based on the co-expression of two immunoglobulin heavy chain-light chain pairs, where the two heavy chains have different specificities (Milstein and Cuello, *Nature*, 305: 537–539 [1983]). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published 13 May 1993, and in Traunecker et al., *EMBO J.*, 10: 3655–3659 (1991).

According to a different and more preferred approach, antibody-variable domains with the desired binding specificities (antibody-antigen combining sites) are fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1), containing the site necessary for light-chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the production of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation.

For further details of generating bispecific antibodies, see, for example, Suresh et al., *Methods in Enzymology*, 121: 210 (1986).

(vii) Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/00373; and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

C. Purification of Antagonists

Techniques used for separating the antagonist(s) from impurities depend on which particular antagonist(s) is being employed. These procedures may include, for example, one or more steps selected from immunoaffinity chromatography, ion-exchange column fractionation (e.g., on DEAE or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the LIF antagonist or endothelin antagonist, and ethanol or ammonium sulfate precipitation. A protease inhibitor may be included in any of the foregoing steps to inhibit proteolysis. Examples of suitable protease inhibitors include phenylmethylsulfonyl fluoride (PMSF), leupeptin, pepstatin, aprotinin, 4-(2-aminoethyl)-benzenesulfonyl fluoride hydrochloride-bestatin, chymostatin, and benzamidine.

D. Hypertrophy Assay

A miniaturized assay is preferably used to assay the suspected antagonist(s) for hypertrophy-inhibiting activity. In this assay the medium used allows the cells to survive at a low plating density without serum. By plating directly into this medium, washing steps are eliminated so that fewer cells are removed. The plating density is important: many fewer cells and the survival is reduced; many more cells and the myocytes begin to self-induce hypertrophy.

The steps involved are:

(a) plating 96-well plates with a suspension of myocytes at a cell density of about $7.5 \times 10^4$ cells per mL in D-MEM/F-12 medium supplemented with at least insulin, transferring and aprotinin;

(b) culturing the cells in the presence of LIF or endothelin;

(c) adding a substance to be assayed (the suspected antagonist of LIF or endothelin);

(d) culturing the cells with the substance; and (e) measuring for hypertrophy.

The medium can be supplemented with additional elements such as EGF that ensure a longer viability of the cells, but such supplements are not essential. D-MEM/F-12 medium is available from Gibco BRL, Gaithersburg, Md., and consists of one of the following media:

| Component | 11320 1 × Liquid (mg/L) | 11321 1 × Liquid (mg/L) | 11330 1 × Liquid (mg/L) | 11331 1 × Liquid (mg/L) | 12400 Powder (mg/L) | 12500 Powder (mg/L) |
|---|---|---|---|---|---|---|
| AMINO ACIDS: | | | | | | |
| L-Alanine | 4.45 | 4.45 | 4.45 | 4.45 | 4.45 | 4.45 |
| L-Arginine.HCl | 147.50 | 147.50 | 147.50 | 147.50 | 147.50 | 147.50 |
| L-Asparagine.H$_2$O | 7.50 | 7.50 | 7.50 | 7.50 | 7.50 | 7.50 |
| L-Aspartic acid | 6.65 | 6.65 | 6.65 | 6.65 | 6.65 | 6.65 |
| L-Cysteine.HCl.H$_2$O | 17.56 | 17.56 | 17.56 | 17.56 | 17.56 | 17.56 |
| L-Cystine.2HCl | 31.29 | 31.29 | 31.29 | 31.29 | 31.29 | 31.29 |
| L-Glutamic acid | 7.35 | 7.35 | 7.35 | 7.35 | 7.35 | 7.35 |
| L-Glutamine | 365.00 | 365.00 | 365.00 | 365.00 | 365.00 | 365.00 |
| Glycine | 18.75 | 18.75 | 18.75 | 18.75 | 18.75 | 18.75 |
| L-Histidine.HCl.H$_2$O | 31.48 | 31.48 | 31.48 | 31.48 | 31.48 | 31.48 |
| L-Isoleucine | 54.47 | 54.47 | 54.47 | 54.47 | 54.47 | 54.47 |
| L-Leucine | 59.05 | 59.05 | 59.05 | 59.05 | 59.05 | 59.05 |
| L-Lysine.HCl | 91.25 | 91.25 | 91.25 | 91.25 | 91.25 | 91.25 |
| L-Methionine | 17.24 | 17.24 | 17.24 | 17.24 | 17.24 | 17.24 |
| L-Phenylalanine | 35.48 | 35.48 | 35.48 | 35.48 | 35.48 | 35.48 |
| L-Proline | 17.25 | 17.25 | 17.25 | 17.25 | 17.25 | 17.25 |
| L-Serine | 26.25 | 26.25 | 26.25 | 26.25 | 26.25 | 26.25 |
| L-Threonine | 53.45 | 53.45 | 53.45 | 53.45 | 53.45 | 53.45 |
| L-Tryptophan | 9.02 | 9.02 | 9.02 | 9.02 | 9.02 | 9.02 |
| L-Tyrosine 2Na 2H$_2$O | 55.79 | 55.79 | 55.79 | 55.79 | 55.79 | 55.79 |
| L-Valine | 52.85 | 52.85 | 52.85 | 52.85 | 52.85 | 52.85 |
| INORGANIC SALTS: | | | | | | |
| CaCl$_2$ anhyd. | 116.60 | 116.60 | 116.60 | 116.60 | 116.60 | 116.60 |
| CuSO$_4$ 5H$_2$O | 0.0013 | 0.0013 | 0.0013 | 0.0013 | 0.0013 | 0.0013 |
| Fe(NO$_3$)$_3$ 9H$_2$O | 0.05 | 0.05 | 0.05 | 0.05 | 0.05 | 0.05 |
| FeSO$_4$ 7H$_2$O | 0.417 | 0.417 | 0.417 | 0.417 | 0.417 | 0.417 |
| KCl | 311.80 | 311.80 | 311.80 | 311.80 | 311.80 | 311.80 |
| MgCl$_2$ | 28.64 | 28.64 | 28.64 | 28.64 | 28.64 | 28.64 |
| MgSO$_4$ | 48.84 | 48.84 | 48.84 | 48.84 | 48.84 | 48.84 |
| NaCl | 6999.50 | 6999.50 | 6999.50 | 6999.50 | 6999.50 | 6999.50 |
| NaHCO$_3$ | 2438.00 | 2438.00 | 2438.00 | 2438.00 | — | — |
| NaH$_2$PO$_4$ H$_2$O | 62.50 | 62.50 | 62.50 | — | 62.50 | 62.50 |
| Na$_2$HPO$_4$ | 71.02 | 71.02 | 71.02 | — | 71.02 | 71.02 |
| ZnSO$_4$7H$_2$O | 0.432 | 0.432 | 0.432 | 0.432 | 0.432 | 0.432 |
| OTHER COMPONENTS: | | | | | | |
| D-Glucose | 3151.00 | 3151.00 | 3151.00 | 3151.00 | 3151.00 | 3151.00 |
| HEPES | — | — | 3574.50 | 3574.50 | 3574.50 | — |
| Na hypoxanthine | 2.39 | 2.39 | 2.39 | 2.39 | 2.39 | 2.39 |
| Linoleic acid | 0.042 | 0.042 | 0.042 | 0.042 | 0.042 | 0.042 |
| Lipoic acid | 0.105 | 0.105 | 0.105 | 0.105 | 0.105 | 0.105 |
| Phenol red | 8.10 | 8.10 | 8.10 | 8.10 | 8.10 | 8.10 |
| Putrescine 2H$_2$O | 0.081 | 0.081 | 0.081 | 0.081 | 0.081 | 0.081 |
| Sodium pyruvate | 55.00 | 55.00 | 55.00 | 55.00 | 55.00 | 55.00 |
| VITAMINS: | | | | | | |
| Biotine | 0.0035 | 0.0035 | 0.0035 | 0.0035 | 0.0035 | 0.0035 |
| D-Ca pantothenate | 2.24 | 2.24 | 2.24 | 2.24 | 2.24 | 2.24 |
| Choline chloride | 8.98 | 8.98 | 8.98 | 8.98 | 8.98 | 8.98 |
| Folic acid | 2.65 | 2.65 | 2.65 | 2.65 | 2.65 | 2.65 |
| i-Inositol | 12.60 | 12.60 | 12.60 | 12.60 | 12.60 | 12.60 |
| Niacinamide | 2.02 | 2.02 | 2.02 | 2.02 | 2.02 | 2.02 |
| Pyridoxal HCl | 2.00 | — | 2.00 | — | 2.00 | 2.00 |
| Pyridoxine HCl | 0.031 | 2.031 | 0.031 | 2.031 | 0.031 | 0.031 |
| Riboflavin | 0.219 | 0.219 | 0.219 | 0.219 | 0.219 | 0.219 |
| Thiamine HCl | 2.17 | 2.17 | 2.17 | 2.17 | 2.17 | 2.17 |
| Thymidine | 0.365 | 0.365 | 0.365 | 0.365 | 0.365 | 0.365 |
| Vitamin B$_{12}$ | 0.68 | 0.68 | 0.68 | 0.68 | 0.68 | 0.68 |

The preferred hypertrophy assay comprises:

(a) pre-coating the wells of 96-well tissue culture plates with a medium containing calf serum, preferably D-MEM/F-12 medium containing 4% fetal calf serum, wherein preferably the wells are incubated with the medium for about eight hours at about 37° C.;

(b) removing the medium;

(c) plating a suspension of myocytes in the inner 60 wells at 7.5×10$^4$ cells per mL in D-MEM/F-12 medium supplemented with insulin, transferring and aprotinin;

(d) culturing the myocytes for at least 24 hours in the presence of LIF or endothelin;

(e) adding the test substance;

(f) culturing the cells with the test substance (preferably for about 24–72 hours, more preferably for about 48 hours); and (g) evaluating hypertrophy, preferably after crystal violet stain, by microscopic examination.

Preferably the medium used in step (c) is a serum-free medium also containing penicillin/streptomycin (pen/strep) and glutamine. Most preferably, the medium contains 100 mL D-MEM/F-12, 100 μL transferring (10 mg/mL), 20 μL insulin (5 mg/mL), 50 μL aprotinin (2 mg/mL), 1 mL pen/strep (JRH Biosciences No. 59602-77P), and 1 mL L-glutamine (200 mM).

Another method for assaying hypertrophy involves measuring for atrial natriuretic peptide (ANP) release by means of an assay that determines the competition for binding of $^{125}$I-rat ANP for a rat ANP receptor A-IgG fusion protein. The method suitable for use is similar to that used for determining GP130 using a CD4-IgG fusion protein described by Chamow et al., *Biochemistry*, 29: 9885–9891 (1990).

2. Therapeutic Compositions and Administration of Antagonists

Antagonists to LIF alone or in combination with antagonists to endothelin are believed to find use as drugs for in vivo treatment of mammals (e.g., animals or humans) experiencing heart failure, so as to prevent or lessen hypertrophic effects. For example, the LIF antagonist alone or with the endothelin antagonist may be useful in treating congestive heart failure in cases where ACE inhibitors cannot be employed or are not as effective.

Therapeutic formulations of antagonist(s) for treating heart disorders are prepared for storage by mixing the antagonist(s) having the desired degree of purity with optional physiologically acceptable carriers, excipients, or stabilizers (*Remington's Pharmaceutical Sciences*, 16th edition, Oslo, A., Ed., [1980]), in the form of lyophilized cake or aqueous solutions. Acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics, or polyethylene glycol (PEG). The antagonist(s) are also suitably linked to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

The antagonist(s) to be used for in vivo administration must be sterile. This is readily accomplished by filtration through sterile filtration membranes, prior to or following lyophilization and reconstitution. The antagonist(s) ordinarily will be stored in lyophilized form or in solution.

Therapeutic antagonist compositions generally are placed into a container having a sterile access port, for example, an intravenous solution bag or vial having a stopper pierceable by a hypodermic injection needle.

The antagonist(s) administration is in a chronic fashion using, for example, one of the following routes: injection or infusion by intravenous, intraperitoneal, intracerebral, intramuscular, intraocular, intraarterial, or intralesional routes, orally if an orally active small molecule is employed, or using sustained-release systems as noted below. Antagonist (s) is administered continuously by infusion or by periodic bolus injection if the clearance rate is sufficiently slow, or by administration into the blood stream or lymph. The preferred administration mode is directly to the heart, so as to direct the molecule to the source and minimize side effects of the antagonists.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate)as described by Langer et al., *J. Biomed. Mater. Res.*, 15: 167–277 [1981] and Langer, *Chem. Tech.*, 12: 98–105 [1982] or poly (vinylalcohol)), polylactides (U.S. Pat. No. 3,773,919, EP 58,481), copolymers of L-glutamic acid and gamma ethyl-L-glutamate (Sidman et al., *Biopolymers*, 22: 547–556 [1983]), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid (EP 133, 988). The antagonist(s) also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, supra.

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release antagonist(s) compositions also include liposomally entrapped antagonist(s). Liposomes containing antagonist(s) are prepared by methods known per se: DE 3,218,121; Epstein et al., *Proc. Natl. Acad. Sci. USA*, 82: 3688–3692 (1985); Hwang et al., *Proc. Natl. Acad. Sci. USA*, 77: 4030–4034 (1980); EP 52,322; EP 36,676; EP 88,046; EP 143,949; EP 142,641; Japanese patent application 83–118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal antagonist therapy. A specific example of a suitable sustained-release formulation is in EP 647,449.

An effective amount of antagonist(s) to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage of LIF antagonist used alone might range from about 1 μg/kg to up to 100 mg/kg of patient body weight or more per day, depending on the factors mentioned above, preferably about 10 μg/kg/day to 10 mg/kg/day.

If the two antagonists are administered together, they need not be administered by the same route, nor in the same formulation. However, they can be combined into one formulation as desired. Both antagonists can be administered to the patient, each in effective amounts, or each in amounts that are sub-optimal but when combined are effective. Preferably such amounts are about 10 μg/kg/day to 10 mg/kg/day of each. In another preferred embodiment, the administration of both antagonists is by injection using, e.g., intravenous or subcutaneous means, depending on the type of antagonist employed. Typically, the clinician will administer the antagonist(s) until a dosage is reached that achieves the desired effect for treatment of the heart dysfunction. For example, the amount would be one which decreases hypertrophy, increases ventricular contractility, and decreases peripheral vascular resistance or ameliorates or treats conditions of similar importance in congestive heart failure patients, thus obtaining the result desired in the continuum of equilibria between growing and shrinking of cardiac muscle tissue. The progress of this therapy is easily monitored by conventional assays.

The two types of antagonists, if used together, may be formulated together in an appropriate carrier vehicle to form a pharmaceutical composition that preferably does not contain cells. In one embodiment, the buffer used for formulation will depend on whether the composition will be employed immediately upon mixing or stored for later use, since long-term storage may bring into issue stability such as solubility and aggregation that can be addressed by altering the pH. The final preparation may be a stable liquid or lyophilized solid.

The antagonist(s) optionally is combined with or administered in concert with other agents for treating congestive heart failure, including ACE inhibitors, CT-1 inhibitors, hGH, and/or IGF-I.

The effective amounts of such agents, if employed, will be at the physician's or veterinarian's discretion. Dosage administration and adjustment is done to achieve the best management of congestive heart failure and ideally takes into account use of diuretics or digitalis, and conditions such as hypotension and renal impairment. The dose will additionally depend on such factors as the type of drug used and the specific patient being treated. Typically the amount employed will be the same dose as that used if the drug were to be administered without antagonist; however, lower doses may be employed depending on such factors as the presence of side-effects, the condition being treated, the type of patient, and the type of antagonist and drug, provided the total amount of agents provides an effective dose for the condition being treated.

Thus, for example, in the case of ACE inhibitors, a test dose of enalapril is 5 mg, which is then ramped up to 10–20 mg per day, once a day, as the patient tolerates it. As another example, captopril is initially administered orally to human patients in a test dose of 6.25 mg and the dose is then escalated, as the patient tolerates it, to 25 mg twice per day (BID) or three times per day (TID) and may be titrated to 50 mg BID or TID. Tolerance level is estimated by determining whether decrease in blood pressure is accompanied by signs of hypotension. If indicated, the dose may be increased up to 100 mg BID or TID. Captopril is produced for administration as the active ingredient, in combination with hydrochlorothiazide, and as a pH stabilized core having an enteric or delayed release coating which protects captopril until it reaches the colon. Captopril is available for administration in tablet or capsule form. A discussion of the dosage, administration, indications and contraindications associated with captopril and other ACE inhibitors can be found in the *Physicians Desk Reference*, Medical Economics Data Production Co., Montvale, N.J. 2314–2320 (1994).

The following examples are offered by way of illustration and not by way of limitation. The disclosures of all citations in the specification are expressly incorporated herein by reference.

EXAMPLE I

1. Materials and Methods

A. Materials

The collagenase CLS 2 was from Worthington (Freehold N.J.) and the Percoll™ from Pharmacia Biotech AB (Uppsala, Sweden). The culture media and supplements were from GIBCO BRL (Grand Island, N.Y.). The aprotinin and crystal violet were from Sigma, St. Louis, Mo. The crystallized bovine serum albumin (BSA) was from ICN Biomedicals (Aurora, Ill.). The Falcon 96 well plates were from Becton Dickenson (Oxnard, Calif.) and the Lab Tek™ chamber slides from Nunc (Naperville, Ill.). Human/porcine endothelin-1 was from American Peptides (Sunnyvale, Calif.). Mouse and human LIF have been recombinantly produced. See Rose and Todaro, WO 93/05169 and Kim et al., supra. The recombinant murine LIF used herein was from Genzyme, Mass; the anti-human LIF monoclonal antibodies were obtained as described by Kim et al., supra, and WO 93/23556, supra. The BQ-123 was obtained as described by Ihara et al., *Life Science*, supra; JP 51–94254A, supra; Webb et al., supra); and the ANP and the ANP-receptor IgG fusion protein were obtained as described by Chamow et al., supra.

B. Myocyte Culture and Hypertrophy Assay

Neonatal rat cardiac ventricular myocytes were cultured in 96- well plates as described by Pennica et al., supra. Briefly, myocytes were isolated from one-day-old Sprague-Dawley rats by a series of collagenase digestions followed by Percoll™ gradient purification. Iwaki et al., *J Biol Chem.*, 265: 13809–13817 (1990). The myocytes, which band at the lower gradient interface, were collected, washed twice, and re-suspended in D-MEM/F12 medium with 15% (vol/vol) fetal calf serum. The cells were diluted into serum-free D-MEM/F12 medium supplemented with 10 μg/mL transferring, 1 μg/mL insulin, 1 μg/mL aprotinin, 2-mmol/L glutamine, 100 U/mL penicillin G, and 100 μg/mL streptomycin (assay medium) to a final density of $7.5 \times 10^4$ cells per mL. The final serum concentration of this assay medium with cells was<0.1%. Myocytes were plated 200 μL per well in 96-well, flat-bottomed plates that had previously been coated with D-MEM/F12 medium with 4% (vol/vol) fetal calf serum for 8 hours at 37° C. After 24 hours at 37° C. in 5% $CO_2$, test substances were added. Forty-eight hours after the test substances were added, the cells were fixed and stained with 0.5% (wt/vol) crystal violet in methanol and formaldehyde, and the hypertrophy was scored on a scale of 1 to 7 by microscopic evaluation. Untreated cells were used as the negative control and scored as a 3. Toxic effects were scored from 0 to 2. The positive control in each assay was 100 μmol/L phenylephrine, which was scored as 7.

C. Non-myocyte Culture

The band at the upper gradient interface is enriched for non-myocytes in the procedure described above. They were collected, washed twice, and re-suspended in D-MEM/F12 medium with 10% fetal calf serum (30 mL/50 hearts) and plated in T75 flasks (2/50 hearts). After one hour at 37° C. in 5% CO2, the flasks were gently swirled and the medium was replaced. After 4 days in culture the cells were trypsinized and re-plated at $4 \times 10^5$ cells per mL in T25 flasks (5 mL/flask). Almost all of the contaminating myocytes are destroyed by this procedure. After 5 days in culture, the cells were washed twice in serum-free D-MEM/F12 medium, and conditioning medium (assay medium with 1 mg/mL BSA) was added. The conditioned medium was removed after 24 hours, centrifuged to remove cells and debris, and stored at 4° C.

D. ANP Measurements

Rat ANP concentrations were determined by competition for the binding of rat $^{125}$I-ANP for a rat ANP receptor A-IgG fusion protein. Chamow et al., supra.

E. Endothelin Measurements

Endothelin concentrations were determined with the Amersham Endothelin 1,2 (high sensitivity) assay system (Amersham, Arlington Heights, Ill.).

F. LIF Measurements

The LIF sandwich ELISA was performed as described by Kim et al., supra, with the following modifications. After the microtiter plates were coated overnight with Mab D4.16.9 (to human LIF), blocked with 0.5% (wt/vol) BSA and washed, the murine LIF standards and samples were added and the plates incubated for 2 hours at room temperature. Then biotinylated (with Pierce ImmunoPur™ Sulfo-NHS-Biotin™) Mab D62.3.2 (to human LIF) was added and the plates were incubated at room temperature for 1 hour. The plates were washed, streptavidin-peroxidase conjugate (Boehringer-Mannheim Biochemicals, Indianapolis, Ind.) was added, and the plates were incubated for 30 minutes at room temperature. The plates were washed and the peroxidase substrate TMB (tetramethylbenzidine) (Kirkegaard and Perry, Gaithersburg Md.) was added. Color development was stopped after 10 minutes by the addition of H3PO4. The absorbance at 450 nm was determined using a microtiter plate reader. An estimate of the concentration of the rat LIF in the NCM was determined by comparison to a murine LIF standard curve.

G. Immunocytochemistry;

The myocytes were plated in 4-chamber Lab Tek™ glass chamber slides pre-costed for 8 hours with 4% (vol/vol) fetal calf serum in D-MEM/F12 medium and cultured for 24 hours. They were exposed to test substances for 48 hours and then washed 3× in phosphate buffered saline (PBS) and fixed in 95% (vol/vol) ethanol for 15 minutes. The slides were then washed 3× in PBS with 0.1% (vol/vol) Tween-20™ surfactant, blocked for 30 minutes with it (wt/vol) BSA in PBS with 0.1% Tween-20™ surfactant, and incubated with phallacidin conjugated to BODIPY FL™ brand reagent (10 μg/mL in 1% BSA in PBS) (Molecular Probes, Eugene Oreg.) for 40 minutes to stain the f-actin present in the contractile fibers. The slides were then washed 3× with PBS in 0.1% Tween-20™ surfactant. Images of the phallacidin-stained cells were acquired on a Ultima™ laser-scanning confocal microscope (Meridian Instruments, Okemos, Mich.). A 1.4 NA 60X ™ oil-immersion objective was utilized coupled with 488-nm excitation, with the resulting fluorescence measured following a 525-nm long-pass filter. Data were collected at a horizontal and vertical resolution of 0.2 μm and a z-resolution of 0.5 μm. Each data point was collected as an average of 200 measurements. The final images were constructed with a maximum fluorescence projection algorithm by compressing the multiple z or depth images into a single two-dimensional representation.

The non-myocytes were plated in 4-chamber Lab Tek™ glass chamber slides, cultured for 5 days, washed 3× with PBS and fixed in 95% ethanol for 15 minutes. The slides were washed 3× in PBS, blocked for 30 minutes with 1% BSA in PBS with 0.1% (vol/vol) Triton X-100™ surfactant, and incubated with the following primary antibodies for 2 hours: (1) monoclonal anti-tropomysin (sarcomeric) (Sigma, St. Louis, Mo.) 1:50 to stain for myocytes, (2) monoclonal anti-alpha smooth muscle actin (Sigma) 1:2500 to stain for fibroblast-like cells, and (3) rabbit anti-human Von Willebrandt Factor (DAKO, Carpenteria, Calif.) 1:500 to stain for endothelial cells. After 3 washes with PBS, the slides were incubated with the appropriate fluorescein-conjugated secondary antibodies (Sigma) 1:200 for 45 minutes and washed 3× with PBS.

2. Results

A. Production of Hypertrophy Activity by Cultured Cardiac Non-myocytes

After exposure to 50% (vol/vol) NCM for 48 hours, neonatal rat ventricular myocytes became enlarged (hypertrophy score 7) compared to untreated cells (hypertrophy score 3), with increased organization of contractile fibers. The increase in myocyte cell size, expressed as hypertrophy score, is dose dependent (FIG. 1A) and is accompanied by an increase in ANP production (FIG. 1B). The hypertrophic activity in the NCM accumulates rapidly up to 5 hours and peaks by 24 hours (FIG. 2). A seeding density of 0.2 to 0.4 million cells per mL is necessary for maximal activity.

Figure 3A:
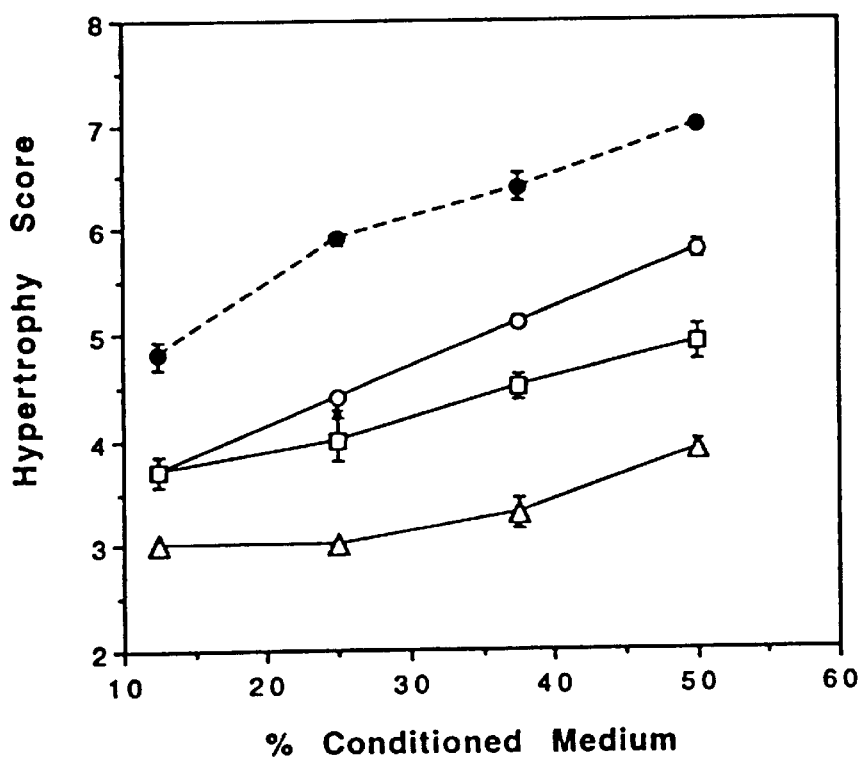
FIG. 3 shows the effect of BQ-123, LIF monoclonal antibody (Mab) D62.3.2 and their combination on myocyte hypertrophy induced by rat neonatal cardiac NCM. Myocytes were treated with NCM (solid circles), NCM and 100 $\mu$mol/L BQ-123 (open circles), NCM and 50 $\mu$g/mL LIF Mab D62.3.2 (open squares) NCM and 100 $\mu$mol/L BQ-123 and 50 $\mu$g/mL LIF Mab D62.3.2 (open triangles). The culture medium was assayed for ANP (FIG. 3B) and the cells were stained and scored for hypertrophy (FIG. 3A). The data in FIG. 3A represent the mean and standard error of three experiments done in duplicate and assayed in duplicate. *p value<0.05 by analysis of co-variance. The data in FIG. 3B represent one experiment done in triplicate and assayed in duplicate.
Figure 3B:
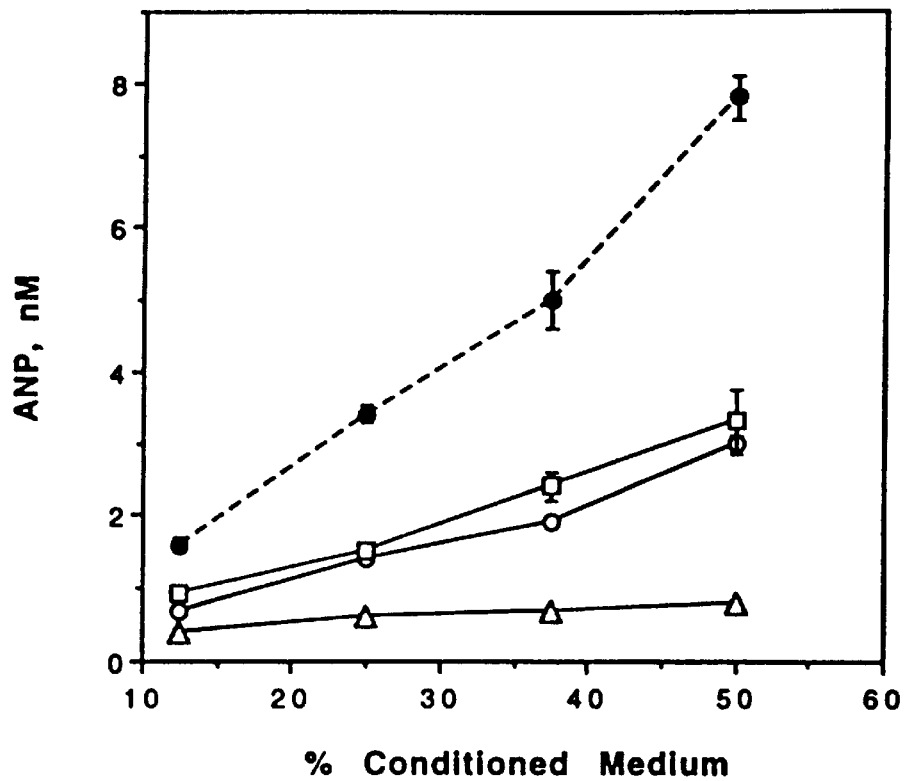
Figure 4A:
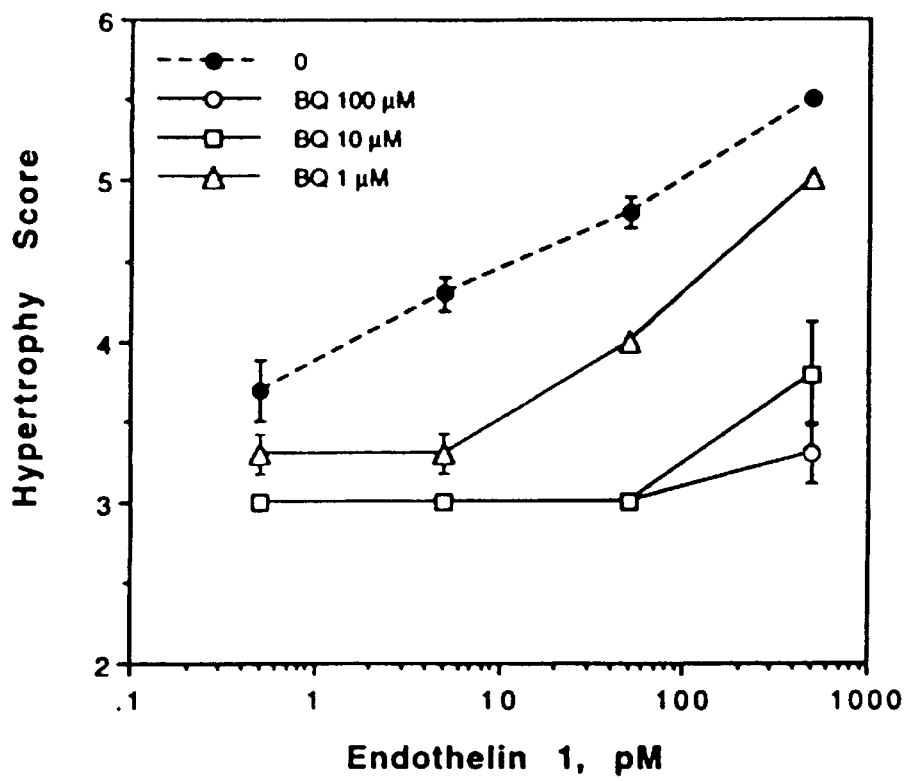
FIGS. 4A–4D depict the effect of BQ-123 on cardiac myocyte hypertrophy induced by endothelin-1, mouse LIF, phenylephrine, and CT-1. Cultured rat neonatal cardiac myocytes were treated with BQ-123 at 0 $\mu$mol/L (solid circles), 100 $\mu$mol/L (open circles), 10 $\mu$mol/L (open squares), and 1 $\mu$mol/L (open triangles) in the presence of endothelin-1 (FIG. 4A), mouse LIF (FIG. 4B), phenylephrine (FIG. 4C), and CT-1 (FIG. 4D). The data represent the mean and standard error of three experiments done in duplicate and assayed in duplicate.
Figure 4B:
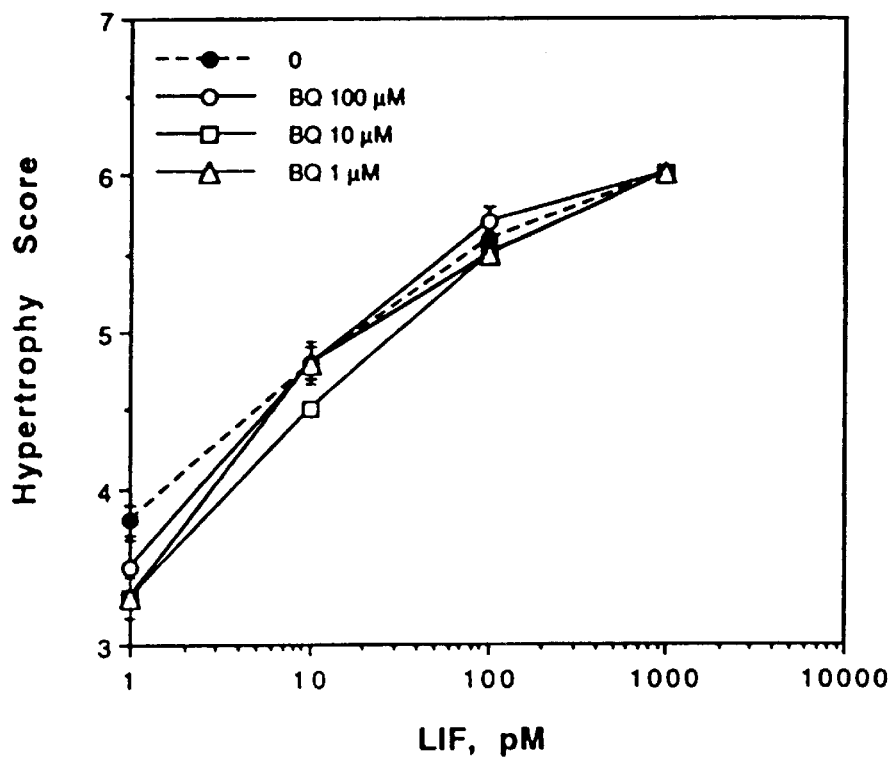
Figure 4C:
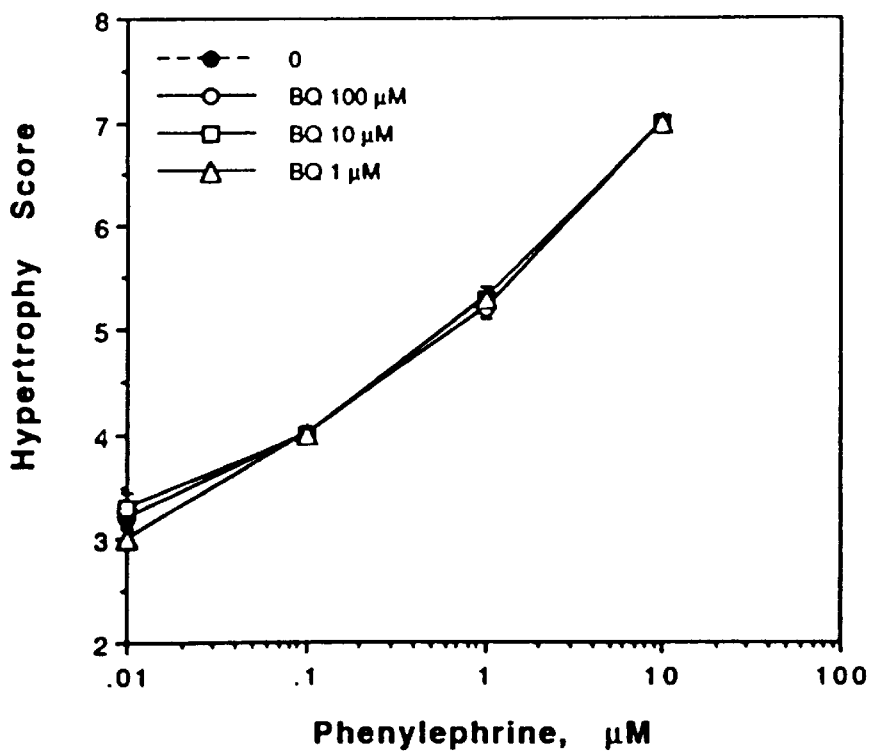
Figure 4D:
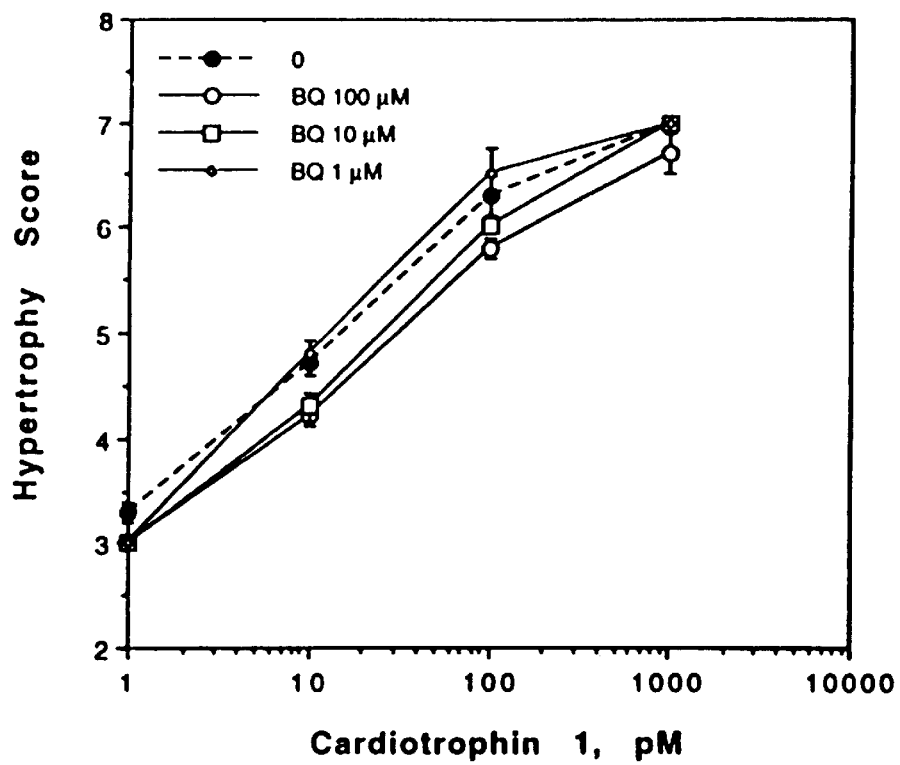
Figure 5A:
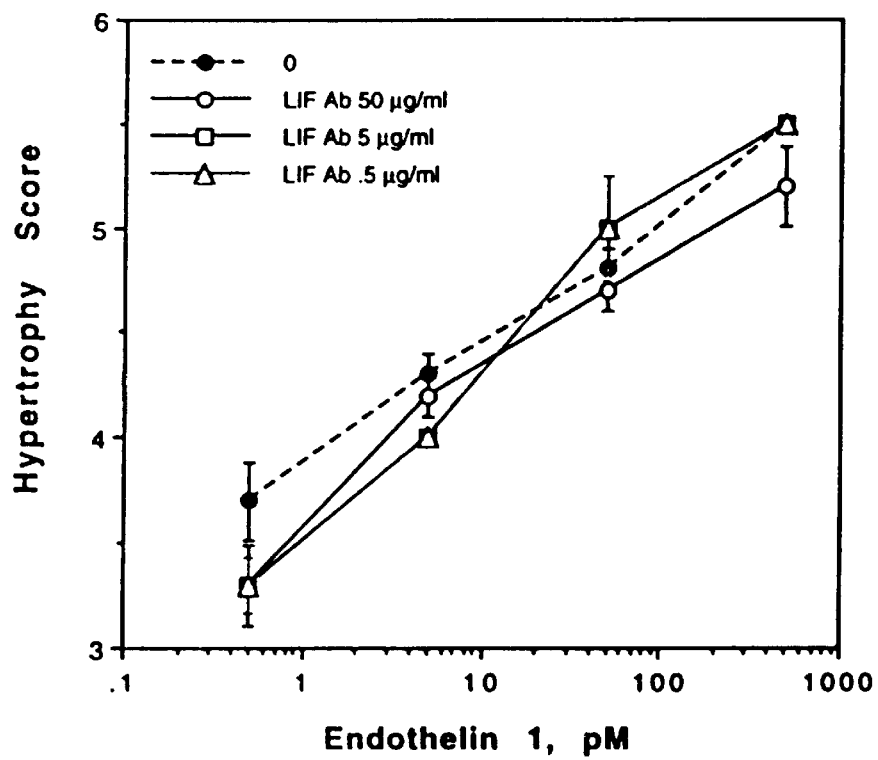
FIGS. 5A–5D depict the effect of LIF Mab D62.3.2 on cardiac myocyte hypertrophy induced by endothelin-1, mouse LIF, phenylephrine, and CT-1. Cultured neonatal rat cardiac myocytes were treated with LIF Mab D62.3.2 at 0 $\mu$g/mL (solid circles), 50 $\mu$g/mL (open circles), 5 $\mu$g/mL (open squares), and 0.5 $\mu$g/mL (open triangles) in the presence of endothelin-1 (FIG. 5A), mouse LIF (FIG. 5B), phenylephrine (FIG. 5C), and CT-1 (FIG. 5D). The data represent the mean and standard error of three experiments done in duplicate and assayed in duplicate.
Figure 5B:
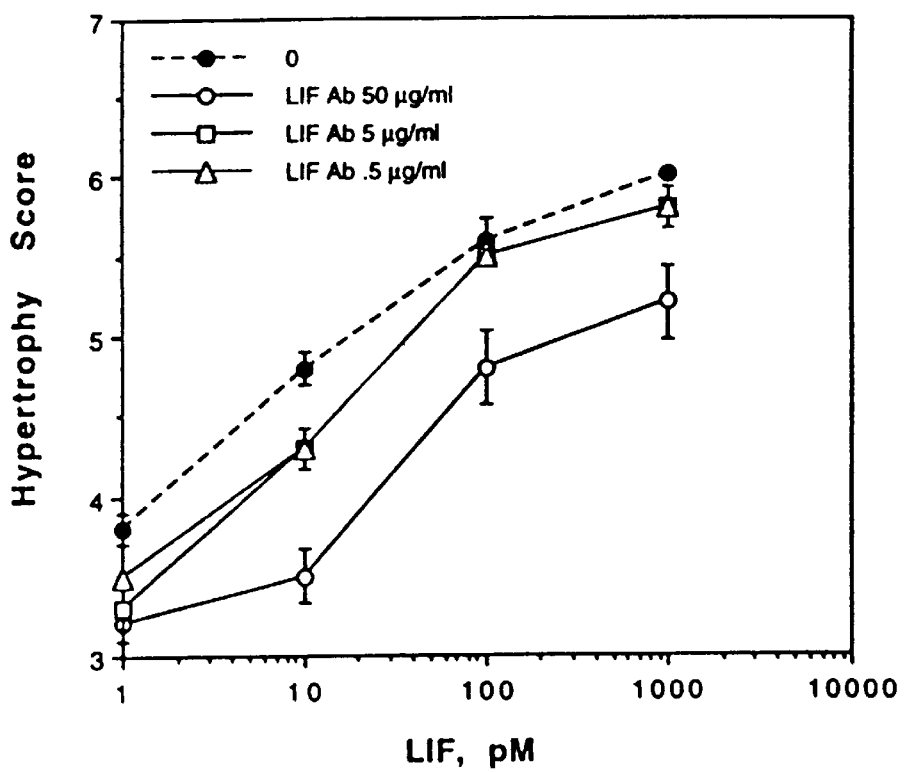
Figure 5C:
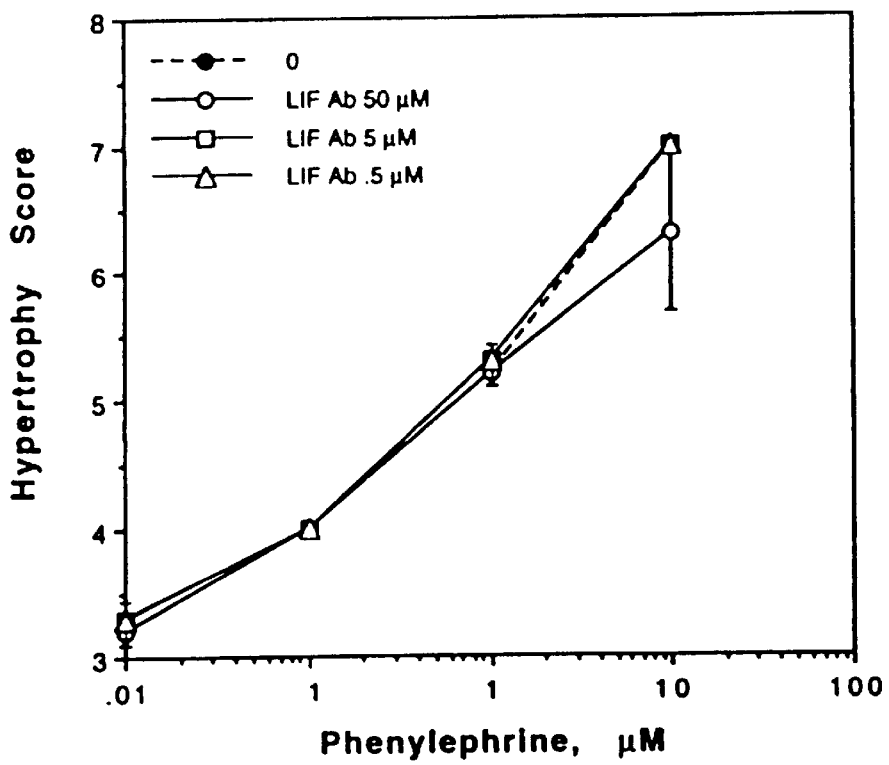
Figure 5D:
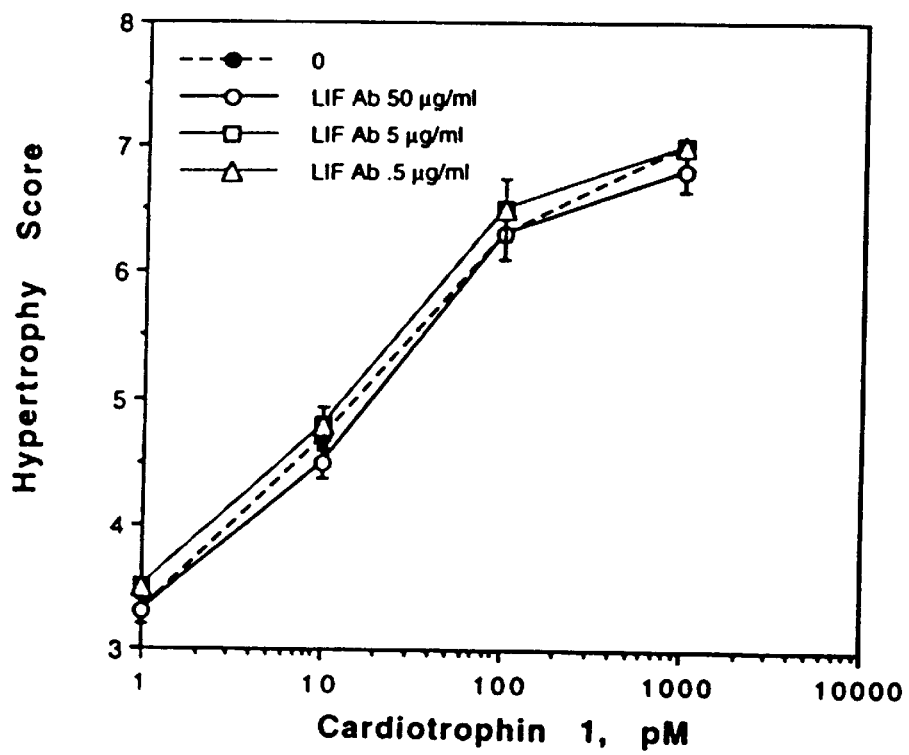

B. Inhibition of Non-myocyte Conditioned Medium Hypertrophy Activity by Endothelin Receptor Blocker and LIF Monoclonal Antibody The endothelin A receptor blocker BQ-123 and a Mab to recombinant human LIF (Mab D62.3.2) each partially inhibited the NCM hypertrophy activity. When both were added together, the activity was almost completely blocked (FIG. 3). The BQ-123 and the LIF Mab appeared to be specific inhibitors. BQ-123 blocked only the hypertrophy activity induced by endothelin-1, not CT-1, mouse LIF (MLIF), or phenylephrine (FIG. 4). The LIF Mab was partially neutralizing for the activity induced by mLIF and did not affect the activity induced by endothelin-1, CT-1 or phenylephrine (FIG. 5). BQ-123 and the LIF Mab by themselves had no effect on myocyte morphology.

The presence of endothelin and LIF in the NCM was confirmed by immunoassay. Endothelin (endothelin-1and -2 and big endothelin) in NCM was measured by radioimmunoassay and averaged 229±10 pmol/L for three preparations. The concentration of LIF in the NCM was estimated using a sandwich ELISA with two anti-human LIF monoclonal antibodies and mouse LIF as the standard. The value obtained for the concentration of LIF using this technique was 190±50 pmol/L for three preparations.

C. Effect of Purified LIF and Endothelin on Cardiac Myocyte Hypertrophy in vitro The typical morphology of the myocytes after a 48-hour exposure to maximal concentrations of purified mLIF and endothelin-1 alone and the combination of the two agents was observed. The cells exposed to LIF tended to be stretched with dendritic-like processes. Those exposed to endothelin were more compact with no processes. Exposure to the combination resulted in a hybrid phenotype with a loss of processes and an increase in size that resembles the morphology resulting from treatment with phenylephrine and NCM.

The organization of the contractile fibers was observed for myocytes which had been stained with fluorescent phallacidin to visualize f-actin. The fibers in the non-treated controls were disorganized and short compared to those in the myocytes, which had hypertrophied. The fibers in the endothelin-treated cells were not organized in parallel, had a tangled appearance, and did not show prominent banding.

Figure 6A:
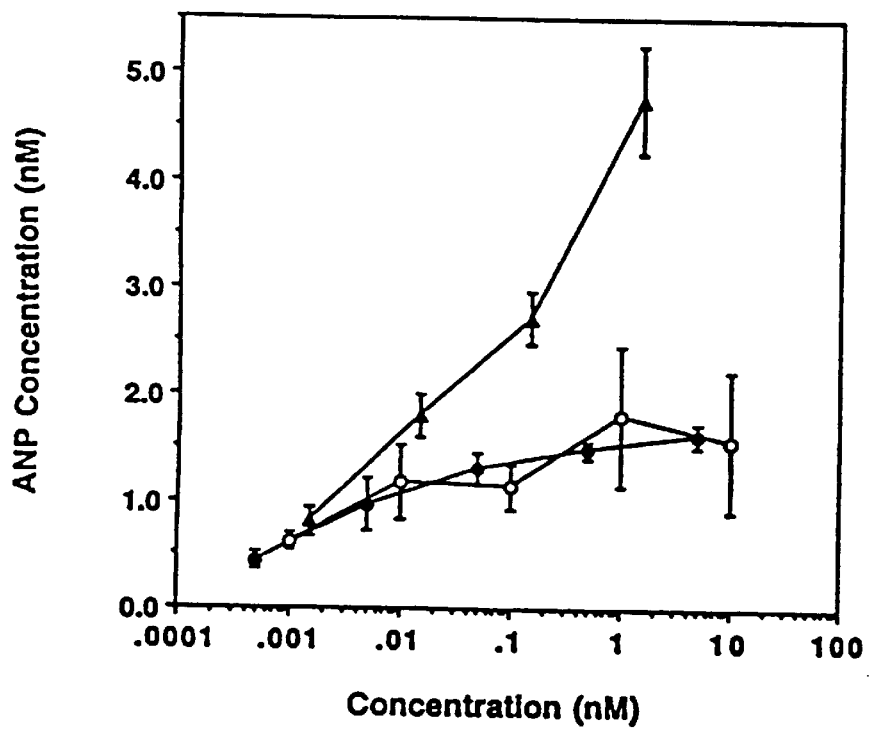
FIG. 6 depicts the effect of LIF and endothelin on cultured neonatal rat cardiac myocyte hypertrophy and ANP production. Myocytes were treated with mouse LIF (open circles), endothelin-1 (solid circles), and a combination of mouse LIF and endothelin-1 (solid triangles). The assay medium was assayed for ANP (FIG. 6A) and the myocytes were stained with crystal violet and scored for cell size (FIG. 6B). The data represent the mean and standard error of three experiments done in duplicate and assayed in duplicate. The concentration of the combination of LIF and endothelin was determined by adding the concentrations of each agent.
Figure 6B:
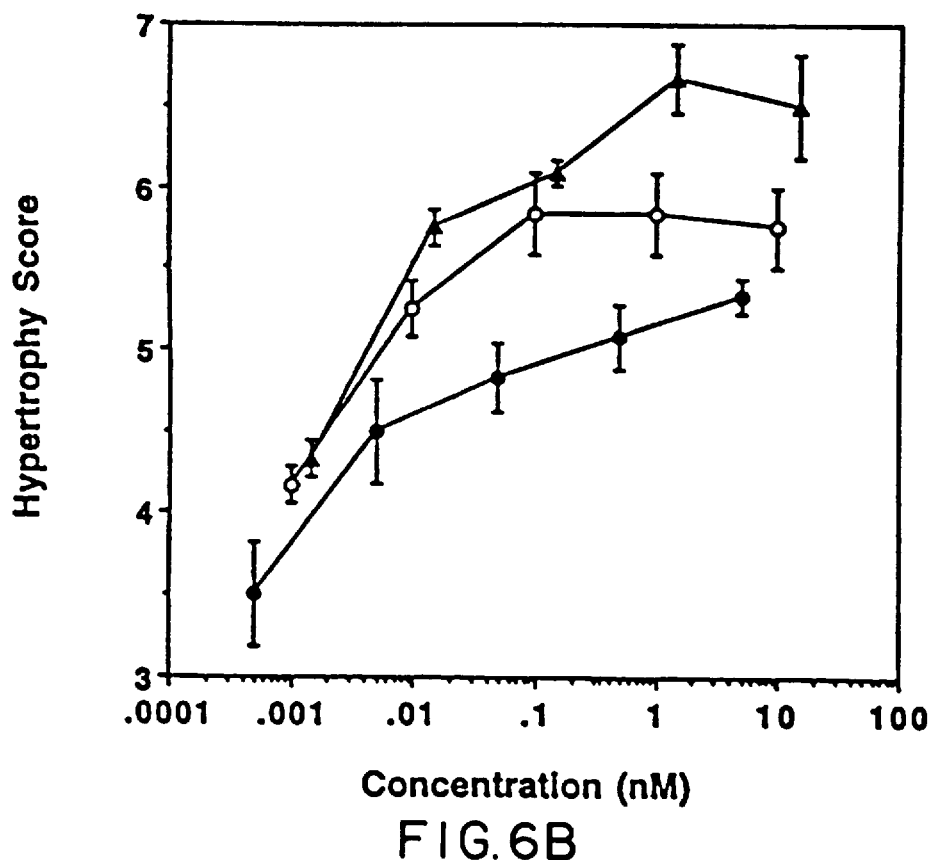

The fibers in the myocytes treated with mLIF, the combination of mLIF and endothelin, and phenylephrine were organized in parallel arrays with prominent banding showing the sarcomeric units. In the mLIF-treated cells the contractile fibers were seen to extend to the tips of the projections. The results in FIG. 6 indicate that LIF and endothelin were additive with respect to ANP production (FIG. 6A), and with respect to cell size, expressed as hypertrophy score (FIG. 6B).

D. Identity of Non-myocytes

Immunocytochemistry studies showed that the majority of the cultured cardiac non-myocytes stained with antibody to smooth muscle actin in a stress fiber pattern. Alpha smooth muscle actin expression was observed in cultured fibroblasts derived from newborn rat cardiac tissue. Brouty-Boye et al., *In Vitro Cell Dev. Biol.*, 28A: 293–296 (1992). The myocytes in their study also expressed this actin isoform and could be distinguished from the fibroblasts by the pattern of staining: stress fiber for fibroblasts vs. a striated pattern for myocytes. A similar stress fiber staining pattern was reported by Long et al., supra, in their study of cardiac non-myocytes. Less than 1% of the non-myocytes were found to be endothelial cells (with an antibody to Von Willebrandt Factor) and myocytes (with an antibody to sarcomeric tropomysin). There was no staining on slides where the primary antibodies had been omitted.

The reagents used in this example to block the endothelin and LIF hypertrophic activity appeared to be specific. BQ-123 blocked only the hypertrophic activity induced by endothelin-1, not CT-1, mouse LIF, or phenylephrine. The radioimmunoassay for endothelin, which measures endothelin-1 and -2 and big endothelin, confirmed the receptor blocker data for the presence of endothelin in the NCM.

The LIF monoclonal antibody used in this example, generated against recombinant human LIF, showed neutralizing activity against the hypertrophy induced by both human and mouse LIF, but not against CT-1-, endothelin-, or phenylephrine-induced hypertrophy. Four monoclonal antibodies were available (Mabs D3.14.1, D4.16.9, D25.1.4, and D62.3.2; deposited with the American Type Culture Collection, 12301 Parklawn Drive, Rockville, Md., on Jun. 23. 1992 and assigned ATCC Accession Numbers HB 11076, HB 11077, HB 11074, and HB 11075, respectively), each of which recognized a different epitope on recombinant human LIF. Three of these (Mabs D4.16.9, D25.1.4, and D62.3.2) neutralized the myocyte hypertrophy induced by mouse and human LIF, and two (Mabs D25.1.4 and D62.3.2) were equipotent in inhibiting the hypertrophy induced by NCM. Mab D3.14.1 did not neutralize the ability of mouse or human LIF to induce myocyte hypertrophy. An approximation of the rat LIF concentration in NCM was made using a sandwich ELISA with two of the monoclonal antibodies which neutralized mouse and human LIF-induced hypertrophic activity and with mouse LIF as a standard. The amino acid sequence of rat LIF is 92% similar to mouse LIF. Gough et al., *Growth Factors,* 7: 175–179 (1992).

In this culture system neither purified LIF nor endothelin alone could induce a maximal hypertrophic response with respect to both myocyte cell size and ANP production, even at nanomolar concentrations. Furthermore, each agent induced a characteristic morphology which was different from that induced by phenylephrine. When LIF and endothelin were combined, however, a maximal hypertrophy was induced in the myocytes which resembled those treated with NCM in cell size, morphology, and contractile fiber organization. The myocytes treated with NCM and BQ-123 resembled those treated with purified LIF, as would be expected if the endothelin activity were blocked. The myocytes treated with NCM and the LIF Mab resembled those treated with purified endothelin-l, as would be expected if the LIF activity were blocked.

The responses induced by LIF and endothelin were additive with respect to both cell size and ANP formation.

Immunofluorescence studies indicate that the non-myocyte cultures in this example contained primarily fibroblast-like cells (which stain with antibodies to smooth muscle actin) with less than 1% endothelial cells and myocytes.

In summary, LIF and endothelin were identified as the factors in cultured cardiac neonatal rat NCM that are responsible for the majority of its hypertrophic activity on cultured cardiac neonatal rat myocytes. The presence of endothelin and LIF was confirmed by immunoassay and found to be in the range of 200 pmol/L. Purified LIF and endothelin induced partial hypertrophic responses with morphologies characteristic for each molecule, and neither factor alone promoted the maximal hypertrophic response seen with the combination. The response to the combination of both agents appeared to be additive with respect to myocyte size, morphology, ANP production, and organization of contractile fibers.

What is claimed is:

1. A method for treating a mammal experiencing heart failure to prevent or lessen hypertrophy comprising administering chronically to a mammal in need of such treatment a therapeutically effective amount of a leukemia inhibitory factor antagonist antibody, wherein the antagonist antibody binds LIF and blocks or prevents interaction between LIF and its cellular receptor.

2. The method of claim 1 wherein the mammal is a human and the antagonist is a human antibody or a humanized antibody.

3. The method of claim 2 wherein the antibody is a monoclonal antibody.

4. The method of claim 1, wherein the LIF binds to a LIF binding region from a monoclonal antibody selected from the group consisting of ATCC HB 11077, HB 11074, and HB 11075.

* * * * *

UNITED STATES PATENT AND TRADEMARK OFFICE
CERTIFICATE OF CORRECTION

PATENT NO.  : 5,837,241
DATED       : November 17, 1998
INVENTOR(S) : Ferrara, King, Luis, Mather and Paoni It is certified that error appears in the above-identified patent and that said Letters Patent is hereby corrected as shown below:

Claim 4,
Line 3, after "of" and before "ATCC," insert -- monoclonal antibodies produced by hybridoma cells deposited under American Type Culture Collection Numbers --.

Signed and Sealed this

Second Day of October, 2001

Attest:

NICHOLAS P. GODICI
*Attesting Officer*  *Acting Director of the United States Patent and Trademark Office*